(12) United States Patent
Kaouk et al.

(10) Patent No.: US 12,322,118 B2
(45) Date of Patent: Jun. 3, 2025

(54) ROBOTIC SURGERY

(71) Applicant: The Cleveland Clinic Foundation, Cleveland, OH (US)

(72) Inventors: Jihad Kaouk, Gates Mills, OH (US); Nicholas Haas, Cleveland, OH (US); Tara Nagle, Cleveland, OH (US); Robb Colbrunn, Hinckley, OH (US); Callan Gillespie, Cleveland, OH (US); Keiran Cantilina, Lakewood, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 464 days.

(21) Appl. No.: 17/725,272

(22) Filed: Apr. 20, 2022

(65) Prior Publication Data

US 2022/0354597 A1   Nov. 10, 2022

Related U.S. Application Data

(60) Provisional application No. 63/177,589, filed on Apr. 21, 2021, provisional application No. 63/177,593, (Continued)

(51) Int. Cl.
*G06T 7/246* (2017.01)
*A61B 34/10* (2016.01)
(Continued)

(52) U.S. Cl.
CPC ............ *G06T 7/248* (2017.01); *A61B 34/10* (2016.02); *A61B 34/20* (2016.02); *A61B 34/30* (2016.02); *G05B 19/4155* (2013.01); *G06T 7/0014* (2013.01); *G06T 7/70* (2017.01); *A61B 2034/102* (2016.02); *A61B 2034/104* (2016.02); *A61B 2034/105* (2016.02); *A61B 2034/107* (2016.02); *A61B 2034/2055* (2016.02); *A61B 2034/2057* (2016.02); (Continued)

(58) Field of Classification Search
CPC ......... G06T 7/248; G06T 7/0014; G06T 7/70; G06T 2207/10012; G06T 2207/10132; A61B 34/10; A61B 34/20; A61B 34/30; A61B 2034/102; A61B 2034/104; A61B 2034/105; A61B 2034/107; A61B 2034/2055; A61B 2034/2057; A61B 2034/2063; A61B 2034/2065; A61B 2562/16; A61B 2034/2051; A61B 2090/378; A61B 2090/3983; A61B 34/32; G05B 19/4155; G05B 2219/50391; G05B 2219/45119; G16H 20/30; G16H 20/40
See application file for complete search history.

(56) References Cited

U.S. PATENT DOCUMENTS

2021/0196382 A1* 7/2021 Mumaw .................. A61B 90/37
2022/0215532 A1* 7/2022 Aghdasi ................ G06T 19/006

* cited by examiner

*Primary Examiner* — Ian Jen
*Assistant Examiner* — Renee LaRose
(74) *Attorney, Agent, or Firm* — McDonald Hopkins LLC

(57) ABSTRACT

Teleoperative, partially automated, and fully automated robotic surgery systems and methods are described herein. These systems and methods relate to at least improvement of robotic movements, three dimensional tracking and pose correction for robots interacting with deformable objections, controlling and optimizing the redundant axis of a seven degree of freedom robotic arm, virtual robotic surgery and simulation, and task coordination and optimization for multi-robot surgery.

12 Claims, 20 Drawing Sheets

Related U.S. Application Data filed on Apr. 21, 2021, provisional application No. 63/177,603, filed on Apr. 21, 2021, provisional application No. 63/177,596, filed on Apr. 21, 2021, provisional application No. 63/177,597, filed on Apr. 21, 2021.

(51) Int. Cl.
| | | |
|---|---|---|
| *A61B 34/20* | (2016.01) | |
| *A61B 34/30* | (2016.01) | |
| *G05B 19/4155* | (2006.01) | |
| *G06T 7/00* | (2017.01) | |
| *G06T 7/70* | (2017.01) | |

(52) U.S. Cl.
CPC ......... *A61B 2034/2063* (2016.02); *A61B 2034/2065* (2016.02); *A61B 2562/16* (2013.01); *G05B 2219/50391* (2013.01); *G06T 2207/10012* (2013.01); *G06T 2207/10132* (2013.01)

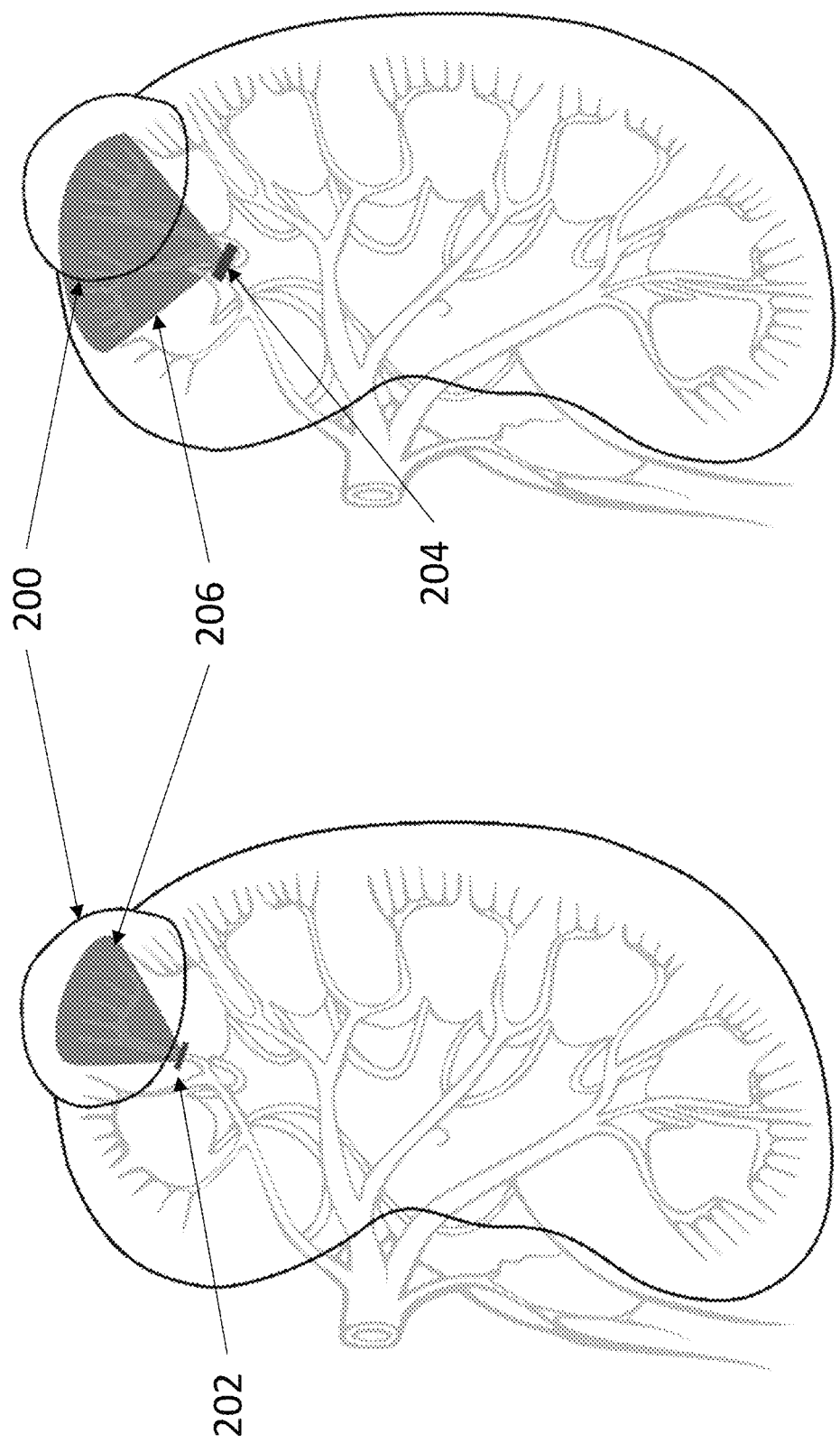

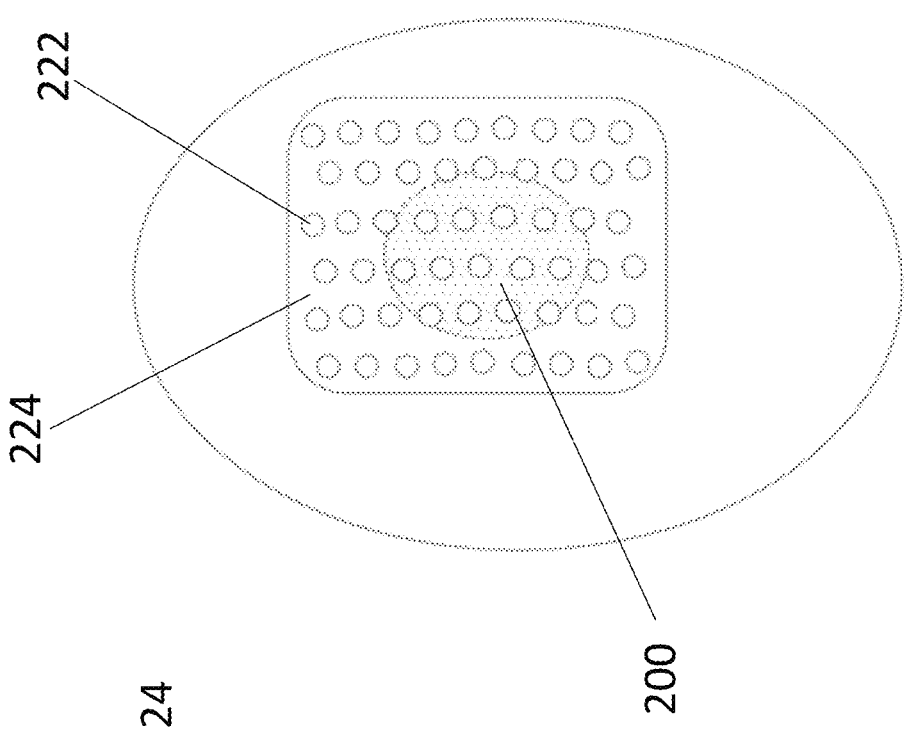
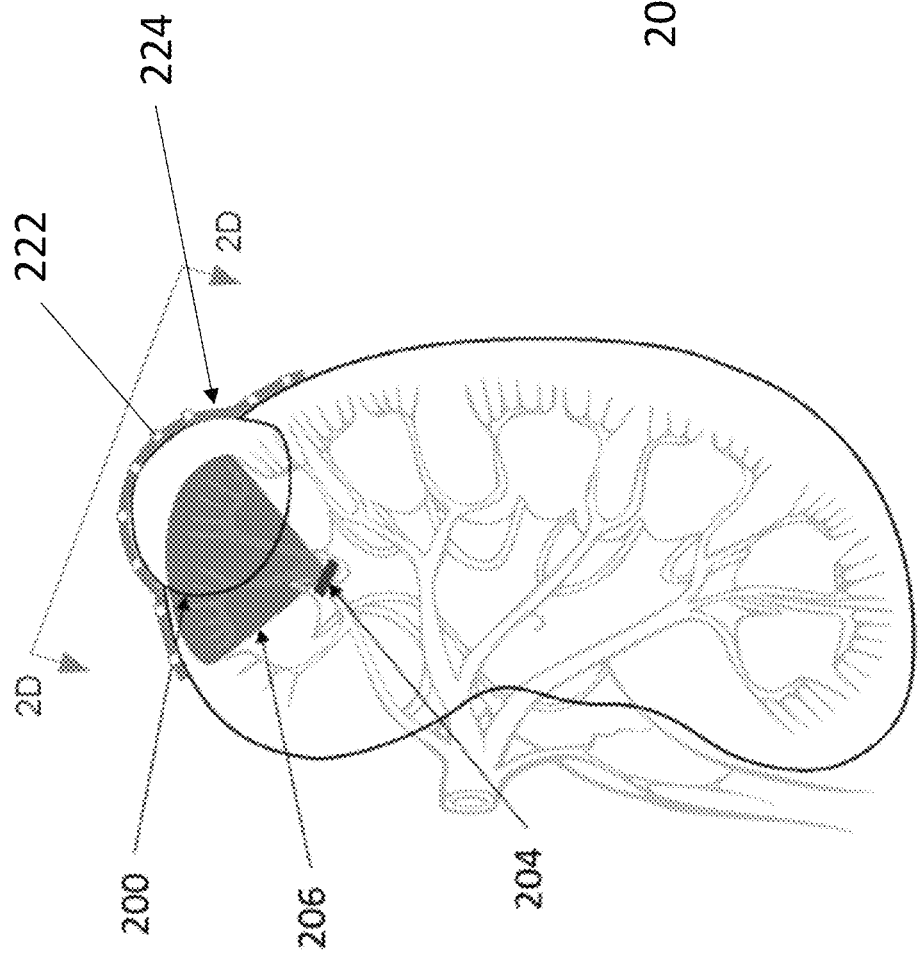
Figure 2E
Figure 2F

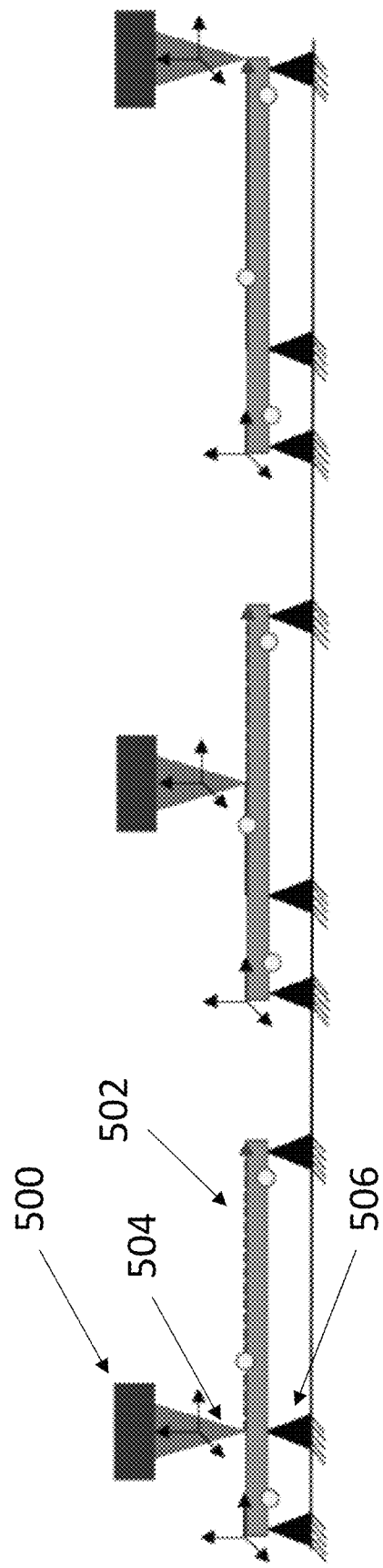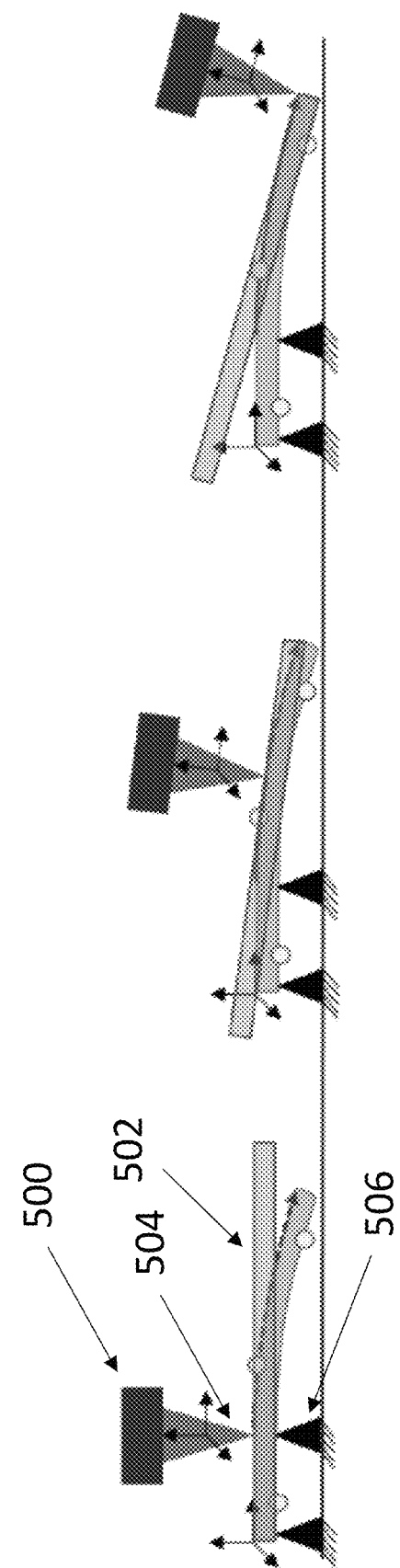
Figure 5A
Figure 5B

ROBOTIC SURGERY

CROSS-REFERENCE TO RELATED APPLICATIONS

This application claims priority to U.S. Provisional Patent Application No. 63/177,589 filed on Apr. 21, 2021, U.S. Provisional Patent Application No. 63/177,593 filed on Apr. 21, 2021, U.S. Provisional Patent Application No. 63/177,596 filed on Apr. 21, 2021, U.S. Provisional Patent Application No. 63/177,597 filed on Apr. 21, 2021, and U.S. Provisional Patent Application No. 63/177,603 filed on Apr. 21, 2021. The entireties of these applications are incorporated herein by reference.

BACKGROUND

Robotic surgery today is essentially purely teleoperative. That is, a human has full control over the motions of a surgical robot, and the robot has almost no ability to make decisions on its own. But by nature, humans are imperfect and thus so is their ability to teleoperate a surgical robot to the full extent of its capabilities. Moreover, a surgical robotic system's potential to perform fully- or partially-autonomous surgical procedures is limited by an inability to adequately design, optimize, and execute safe and effective movements of one or more robots for a given procedure, both pre-operatively and in real time.

BRIEF SUMMARY

According to one example of the present disclosure, a system for evaluating treatment of a surgical target of a patient's soft tissue organ comprises: an imaging system configured to obtain images of the patient's soft tissue organ; and at least one controller configured to: receive a user input of a treatment trajectory on the images to resect a portion of the patient's soft tissue organ; and determine a score related to a function of the patient's soft tissue organ based on the treatment trajectory.

In various embodiments of the above example, the treatment trajectory comprises a cutting trajectory; the images are real time intraoperative images; the score is a percentage of the organ being removed; the at least one controller is further configured to identify a vasculature within the patient's organ within the treatment trajectory, and the score is a function of the portion of the vasculature being removed within the treatment trajectory; the score is a percentage of organ function loss based on the treatment trajectory; the at least one controller is further configured to modify the treatment trajectory based on the determined score; the at least one controller comprises a trained machine learning system configured to receive the treatment trajectory input by the user and to output the score; the trained machine learning system is trained with data comprising treatment trajectories and corresponding surgical outcomes of historical surgical treatments; the score is indicative of expected post-operative function of the organ; determining the score includes determining long-term blood flow through the organ; and/or the organ is a kidney, and determining the score includes determining a post-operative percentage of active nephrons in the kidney.

According to another example of the present disclosure, a method comprises: obtaining an image of a patient's soft-tissue organ through an imaging device; receiving at least one proposed treatment trajectory through a user input device; and generating a score related to a post-operative function of the organ for each of the at least one proposed treatment trajectory.

In various embodiments of the above example, generating the score includes determining an estimate of long-term blood flow through the organ; the organ is a kidney, and generating the score includes determining an estimated post-operative percentage of active nephrons in the kidney; and/or receiving at least one proposed treatment trajectory includes receiving two or more proposed treatment trajectories, and the method further comprises: providing a recommended treatment trajectory based on scores for each of the two or more proposed treatment trajectories.

According to another example of the present disclosure, a non-transitory computer-readable storage medium encoded with instructions executable by a processor of a computing system comprises instructions to: obtain an image of a patient's soft-tissue organ through an imaging device; receive at least one proposed treatment trajectory through a user input device; and generate a score related to a post-operative function of the organ for each of the at least one proposed treatment trajectory.

In various embodiments of the above example, the instructions to generate the score includes instructions to determine an estimate of long-term blood flow through the organ; and/or the organ is a kidney, and the instructions to generate the score includes instructions to determine an estimated post-operative percentage of active nephrons in the kidney.

According to another example of the present disclosure, an apparatus for detecting a surface of a patient's organ comprises: a flexible panel deformable in three dimensions to a surface of the patient's organ; a plurality of spatial tracking sensors secured to the deformable panel; a detector configured to detect at least two of the spatial tracking sensors; and at least one controller configured to identify a location of the at least two spatial tracking sensors.

In various embodiments of the above example, the deformable panel comprises a deformable mesh; the deformable mesh comprises a continuous material forming a grid pattern; the flexible panel comprises a material having fibers, each of the fibers having an elastic length; the panel comprises a bioabsorbable material; the panel comprises a material that is cuttable; the panel is a bag; the panel is expandable; the panel includes micro-barbs configured to maintain the panel onto the surface of the patient's organ; the plurality of spatial tracking sensors comprise at least one optical sensor or ultrasound transmitter; the plurality of spatial tracking sensors includes an array of sensors supported by a region of the panel; the array of sensors has a first density, and the plurality of spatial tracking sensors includes a second array of sensors supported by a second region of the panel, the second array of sensors having a second density greater than the first density; the each of the plurality of spatial tracking sensors is a separate individual sensor; the detector is a stereo-camera system or ultrasound detector; the controller is further configured to generate a sensing grid from the detected spatial sensors and to track tissue deformation of the patient's organ in real time during a surgical procedure; the controller is further configured to register the location of the at least two spatial sensors with a real time operative image; and/or the apparatus further comprises a display configured to display the location of the at least two spatial sensors and a position of an anatomical feature of interest of the patient's organ on the real time operative image.

According to another example of the present disclosure, a method of robotic treatment of a surgical target of a patient's soft tissue organ comprises: obtaining real time intraoperative images of the patient's soft tissue organ; creating a trajectory plan for a surgical instrument to excise or reconstruct a portion of the surgical target of the patient's soft tissue organ; excising the portion of the surgical target using the surgical instrument and based on the instrument trajectory plan; providing real time deformation data indicating real time deformation of an external surface of the patient's soft tissue organ with a plurality of position sensors on the surface of the patient's soft tissue organ; registering the deformation data onto the real time intraoperative images; modifying the trajectory plan in real time based on the real time deformation of the external surface of the patient's soft tissue organ; and controlling the surgical instrument in real time according to the modified trajectory plan.

In various embodiments of the above example, modifying the trajectory plan in real time is a function of both the real time deformation data and an output of a machine learning system indicating future deformation during removal of the patient's soft tissue organ; the method further comprises: robotically positioning an ultrasound probe, and obtaining the real time intraoperative images with the ultrasound probe; the method further comprises: robotically moving the ultrasound probe in real time to change a field of view (FOV) of the ultrasound probe; the ultrasound probe is moved during a surgical procedure; the ultrasound probe is positioned on the surface of the patient's soft tissue organ; the trajectory plan for the surgical target for the surgical instrument to excise the surgical target comprises cutting the surgical target; the trajectory plan for the surgical instrument to excise the surgical target comprises ablating the surgical target; and/or the method further comprises: creating a reconstruction trajectory plan to reconstruct the organ.

According to another example of the present disclosure, a method for robotic excising of a surgical target of a patient's soft tissue organ comprises: obtaining real time intraoperative images of the patient's soft tissue organ; creating an excising plan for a surgical instrument to excise a portion of the surgical target of the patient's soft tissue organ; excising the portion of the surgical target using the surgical instrument and based on the excising plan; providing real time deformation data indicating real time deformation of an external surface of the patient's soft tissue organ; registering the deformation data onto the real time intraoperative images; modifying the excising plan in real time based on the real time deformation of the external surface of the patient's soft tissue organ; and controlling the surgical instrument in real time according to the modified excising plan.

In various embodiments of the above example, the modifying of the excising plan comprises adjusting a trajectory of the surgical instrument; and/or the real time deformation data is obtained with a plurality of position sensors on the surface of the patient's soft tissue organ.

According to another example of the present disclosure, a robotic surgery system comprises: a surgical robot configured to excise a portion of a surgical target of a patient's soft tissue organ based on an instrument trajectory plan; a position sensing apparatus configured to indicate real time deformation of an external surface of the patient's soft tissue organ; a camera configured to obtain real time intraoperative images of the patient's soft tissue organ; and at least one controller configured to: determine real time deformation information of the external surface of the patient's soft tissue organ based on the position sensing apparatus, register the real time determination information to the real time intraoperative images, modify the trajectory plan in real time based on real time deformation of the external surface of the patient's soft tissue organ, and control the surgical robot in real time according to the modified trajectory plan.

In various embodiments of the above example, the position sensing apparatus comprises: a flexible panel deformable in three dimensions to the external surface of the patient's organ, and a plurality of spatial tracking sensors secured to the deformable panel; the system further comprises: an ultrasound probe, wherein the camera is an ultrasound camera of the ultrasound probe; and/or the position sensing apparatus comprises: at least one optical sensor and a stereo-camera system configured to detect the optical sensor, or an ultrasound transmitter and an ultrasound detector configured to detect the ultrasound transmitter.

According to another example of the present disclosure, a surgical system comprises: an imaging system configured to obtain real time intraoperative images of a patient's soft tissue organ; at least one controller configured to generate a rendered virtual model overlayed on to the real time intraoperative images; and a display configured to display the rendered virtual model overlayed on to the real time intraoperative images, wherein the rendered virtual model includes a predefined avoidance region within an anatomy of the patient rendered in a first visual manner, and a predefined acceptable region within the anatomy of the patient rendered in a second visual manner.

In various embodiments of the above example, the rendered virtual model includes a surgical path rendered in the second visual manner or in a third visual manner; the at least one controller is further configured to include a cut margin in the rendered virtual model; the system further comprises a surgical robot, wherein the at least one controller is further configured to determine a location of a surgical instrument of the surgical robot relative to the anatomy of the patient; the system further comprises an output device, wherein the at least one controller is further configured to alert a surgeon via the output device when the location of the surgical instrument is within a predetermined range of the avoidance region; the at least one controller is further configured to control the surgical robot to avoid the avoidance region when the location of the surgical instrument is within a predetermined range of the avoidance region; the system further comprises: a first robotic surgical tool, and a second robotic surgical tool, wherein the at least one controller is further configured to: receive a predefined avoidance region with an anatomy of a patient, receive a real-time location of the first surgical tool, receive a real-time location of the second surgical tool, receive a predefined surgical space outside of the patient, and provide an error warning based upon a real-time location of the second surgical tool relative to the avoidance region, the real-time location of the first surgical tool, and the predefined surgical space outside of the patient; the error warning provides a remedial action to avoid a collision of the second surgical tool with the avoidance region, first surgical tool and/or the predefined surgical space; and/or the system comprises an imaging system obtaining real time intraoperative images of a soft tissue organ of a patient and the virtual model of at least a part of one of the first robotic surgical tool and second robotic surgical tool superimposed on the real time intraoperative image.

According to another example of the present disclosure, a surgical system comprises: a first robotic surgical tool; a second robotic surgical tool; and at least one controller configured to: receive a predefined avoidance region with an anatomy of a patient; receive a real-time location of the first surgical tool; receive a real-time location of the second surgical tool; receive a predefined surgical space outside of the patient; and provide an error warning based upon a real-time location of the second surgical tool relative to the avoidance region, the real-time location of the first surgical tool, and the predefined surgical space outside of the patient.

In various embodiments of the above example, the error warning provides a remedial action to avoid a collision of the second surgical tool with the avoidance region, first surgical tool and/or the predefined surgical space; and/or the system comprises an imaging system obtaining real time intraoperative images of a soft tissue organ of a patient and the virtual model of at least a part of one of the first robotic surgical tool and second robotic surgical tool superimposed on the real time intraoperative image.

BRIEF DESCRIPTION OF THE SEVERAL VIEWS OF THE DRAWING

FIGS. 2A, 2B, 2C, and 2D illustrate example cuts to excise a tumor from a kidney.

FIGS. 2E and 2F illustrate an example mesh having position sensors secured thereto on a kidney.

FIGS. 5A and 5B illustrate a first example effect of deformable bodies on robot trajectory.

DETAILED DESCRIPTION OF THE DRAWING

Figure 1:
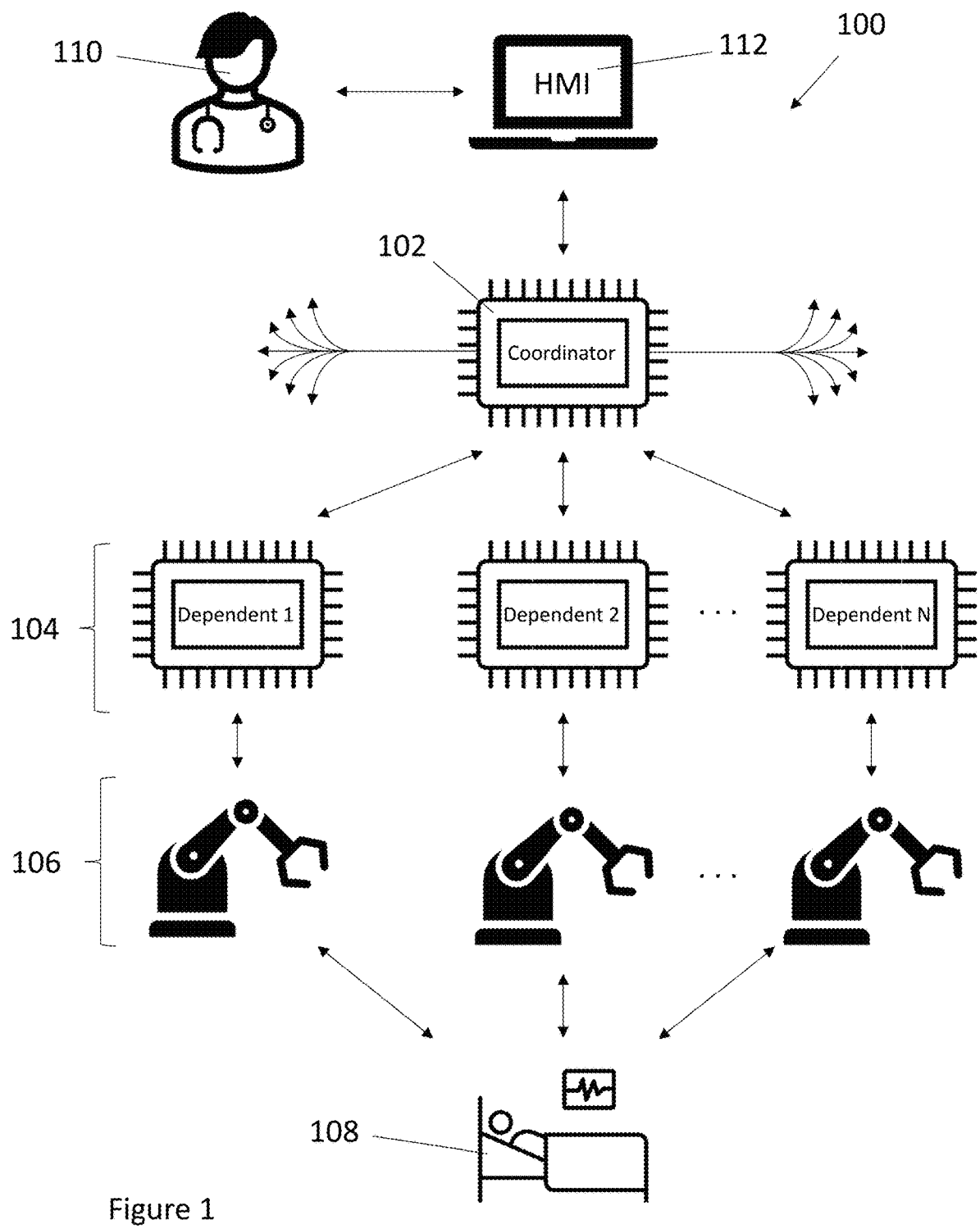
FIG. 1 is a schematic representation of a robotic surgery system, particularly utilizing a coordinator-dependent framework for the coordination of movements of multiple robots.

Briefly, the present disclosure relates to a robotic surgery system 100 and associated methods that address current limitations in the art. As illustrated in FIG. 1, such a system includes one or more controllers 102, 104 (including e.g., one or more processors) that control one more surgical robots 106 according to the methods described herein. The one or more controllers 102, 104 may be located locally or remotely with respect to the robots 106. In the example of FIG. 1, and as described in more detail below, a coordinator controller 102 centrally controls one or more dependent controllers 104, which each individually control a corresponding robot 106. The robots 106 and the controllers 102, 104 may all communicate with each other by various means, including wired and wireless communication. For example, communication may be facilitated by WIFI, Bluetooth, near filed communication, direct peer-to-peer communication, and the like, over a local area network, wide area network, the Internet, and the like. In some specific examples, communication can be via ethernet using a combination of shared network variables, user datagram protocol (UDP), UDP Multicast, and/or transmission control protocol (TCP) communication protocols.

Each surgical robot 106 is configured to interact with a patient 108 with various surgical instruments (e.g., scalpels, clamps, electrodes, and the like). The robots 106 may include one or more servos, stepper motors, and like actuators (linear and/or rotary) for controlling one or more degrees of freedom of an arm holding the instrument. These instruments (and the robots themselves), and sensors associated with the patient 108, may provide feedback to the controllers 102, 104, such that the feedback and other control information is used to determine outputs that effectuate controls of the robots 106 and the instruments. Any of the controllers 102, 104 may be configured to execute any of the below-described aspects of the present disclosure.

Medical personnel (e.g., a surgeon) 110 may interact with and control any of the robots 106 via a human machine interface (HMI) 112. As shown in FIG. 1, the HMI 112 provides interaction with the coordinator controller 102. However, in other embodiments, the medical personnel 110 may interact with any of the robots 106 individually via an associated robot-specific HMI.

It is noted that FIG. 1 represents only one architecture framework for controlling surgical robots. Of course, other architectures may be used within the scope of the present disclosure. Further, any of the noted controllers can be configured to perform any of the methods and analyses (e.g., implement any of the machine learning systems) of the present disclosure. Further it is noted that some embodiments of the present disclosure relate to real time interaction with and control of the robots 106 (e.g., during a surgical procedure). As used herein, the term "real time" refers to a time period in which a person (such as a surgeon or other medical personnel) could not practically perceive any lag. For example, operations conducted in real time may occur within 500 ms of each other, within 450 ms of each other, within 400 ms of each other, or within 200 ms of each other.

According to one aspect of the present disclosure, the robotic surgery systems and methods herein can leverage machine learning and artificial intelligence (or other models and like algorithms executed by one or more processors) to improve surgical planning software and robotic surgical control systems. This is accomplished through the analysis of data collected from both simulated and actual surgical procedures to generate metadata useful for training, evaluation, planning, and the creation of performance reports. More particularly, data from past simulated and executed surgical procedures is input into a machine learning system, which is trained to output feedback to a surgeon and to the robotic system itself. The input data may include information about the surgical procedure (e.g., patient data, type of surgery, and the like), information about the surgical robots (e.g., actuator movements and associated goals of each movement, instrument responses to movements, and the like), and outcomes (e.g., whether movements were successful, whether additional force was required to achieve goal, and the like). The output feedbacks may include suggested movements, control signals for the actuators, notices to a surgeon, and the like.

In other words, the machine learning systems according to this aspect relate to the improvement of surgical planning simulations of the real world, the generation of effective surgical movements, the control of surgical robots, and a human surgeon's creation of planned surgical procedures. Accordingly, the systems address the inability of current robotic surgery systems, surgical simulations systems, and pre-operative planning systems to improve themselves automatically.

In one example, the machine learning system is configured to improve pre-surgical planning simulations. The efficacy of a simulation of a surgical procedure relies on its resemblance to the real world (e.g., the accurate representation of material properties and physics to simulate the cutting action of a scalpel on a kidney). These features of a simulation rely on models that represent real world systems. For example, constitutive models represent real world physical interaction between objects, visual models represent the appearances of objects, and biofunction models can be used to represent the reaction of patient vitals to stimuli. These models can be based on algorithms with numerical constants that can be tuned.

The machine learning system can be trained to analyze recorded robotic surgeries, where the input data comprises extracted information from robotic movements, sensor data, and camera imagery to infer information about the real world. This can help improve the simulation's portrayal of the material properties of the tissues operated on by surgical robots or the response of a patient's heartrate to hemorrhaging. The output of the machine learning system can also control the robot, for example by controlling joint compliance in an improved manner.

More particularly, the trained machine learning system can analyze the aggregate outcome of individual movements or groups of movements of the surgical robot (based on the information from prior surgeries and simulations) to determine if those movements or groups of movements accomplished what was expected. If the analysis results are suboptimal, the trained machine learning system can output more successful movements. For example, for an input of given movements, the trained machine learning system can output a classification of the result of such a movement. Where that classification matches a desired result, the input movement can be accepted as satisfactory. Alternatively, if the classification does not match a desired result, the input movements may be iteratively adjusted until the desired result is output. In some embodiments, the machine learning system may receive an input result and be trained to output corresponding movements to achieve that result.

According to some embodiments, the machine learning systems can be trained to output a change to an organ's functionality resulting from a surgical procedure. This change may be a score of the resulting organ function. For example, the excision of a tumor may be predicted to reduce kidney function by 25% given the desired trajectory plan to remove the tumor. In one particular example, the system is trained to estimate how cuts, excisions, or reconstructions made on an organ will change its functionality based on the principle that cutting an end artery will prevent certain areas of an organ from getting blood flow and, in turn, change the organ's functionality. Further, the system may be trained to consider the time to execute the operation, since a longer procedure may result in more tissue subject to ischemic events (e.g., from clamping of vasculature) that ultimately affect organ function. In addition to consider the above-noted volume loss, vasculature loss, and time of procedure, the system may also be trained to consider cut margins, area of the procedure, and suturing techniques in determining a resulting organ function score. Accordingly, the system can estimate the risk and resulting organ function, and even be trained to suggest new cutting, excision, or reconstruction trajectories.

As seen in the example of FIGS. 2A and 2B, end arteries extend into a tumor 200 of a kidney. A potential cut 202 to excise the tumor 200 shown in FIG. 2A is 1 mm from the tumor 200, while a potential cut 204 shown in FIG. 2B is 2 mm from the tumor 200. The resulting compromised end arteries and the section of the kidney that loses functionality is shown by the shaded region 206. As can be seen, the cut 204 farther away from the tumor 200 results in a cut below a branch in the end artery. This in turn causes the kidney cut according to FIG. 2B to lose a higher percentage of functionality. Considering this, by being trained with data relating to the vasculature structure of the kidney, a machine learning system can output a predicted end functionality of the kidney based on an input cut trajectory.

Figure 2D:
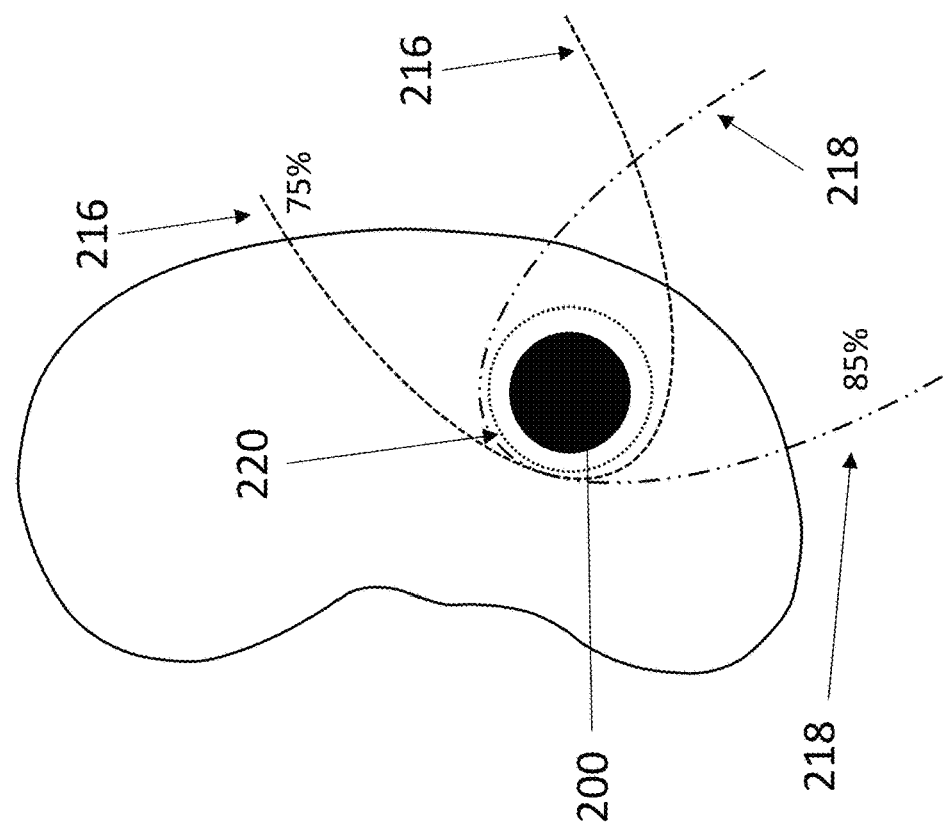
Figure 2C:
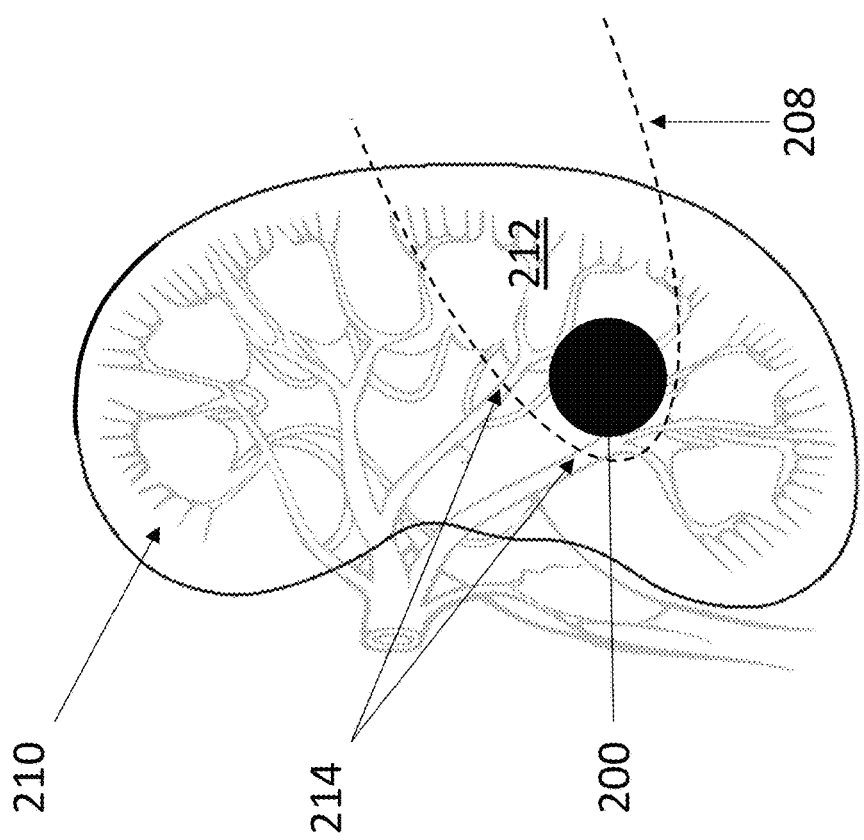

Put another way with reference to FIGS. 2C and 2D, the machine learning system may be trained to determine or calculate a score associated with a proposed treatment trajectory 208 for excising a tumor 200. The score may be indicative of the effectiveness of the proposed treatment trajectory 208, and may be indicative of the remaining post-operative function of the organ. In this regard, the score may be a percentage of function remaining or a percentage of function lost due to the treatment trajectory 208. In another example, the score may be a percentage of the organ remaining or removed. In other examples, the score may be indicative of the parenchymal mass of the organ remaining or removed.

In one example, an imaging system may be used to identify a vasculature 210 within the organ. In this regard, the score may be associated with a percentage of the vasculature 210 that is removed. In certain cases, certain portions of the vasculature 210 may lose post-operative function immediately following the procedure, but that portion of the vasculature may recover function in the long-term. In this regard, the machine learning system may take into account an expectation of such recovery of function in determining the score. Thus, the system may use long-term blood flow through the organ as a factor in determining the score.

The treatment trajectory 208 can result in the cutting of a blood vessel that may supply blood (through smaller blood vessels) to a large portion of the organ, referred to as devascularization. In other words, cutting of a blood vessel may eliminate blood flow to another portion of the organ. For example, cutting off of blood flow through a large blood vessel may affect 50% or more of the organ corresponding to the portion of the vasculature dependent on the large blood vessel being cut. In this regard, the machine learning system may use the information from the imaging system to estimate the percentage of the organ affected by disruption of blood flow through a particular portion of the vasculature.

A user may use the estimate from the controller to determine whether the proposed treatment trajectory 208 is acceptable.

Further, the machine learning system may determine whether and to what extent cutting of a particular blood vessel may affect blood flow to a portion of the organ that is not intended to be excised. For example, the proposed treatment trajectory 208 may be intended to excise a first portion 210 of the organ defined by the interior of the trajectory 208, while intending to preserve a second portion (e.g., the remainder of the organ). However, in some cases, the proposed treatment trajectory 208 may cut a blood vessel 214 which supports blood flow to at least a part of the second portion (e.g., the non-excised portion of the organ). Thus, while a large portion of the parenchymal mass of the organ may be preserved, only a portion of the remaining parenchymal mass may have sufficient blood flow. Thus, the score determined by the controller may reflect not only the percentage of the organ remaining, but also the percentage which will continue to receive blood flow, thereby basing the score on the percentage of functional organ remaining post-operatively.

In some examples, the controller may be provided with multiple proposed treatment trajectories. In such cases, the controller can determine a score for each of the proposed treatment trajectories and, by comparing the scores, provide a recommended treatment trajectory to the user.

In some cases, the controller may determine that the scores for the various proposed treatment trajectories are not acceptable. In such cases, the controller, in conjunction with the machine learning system, may modify a proposed treatment trajectory to achieve an improved score compared to the originally proposed trajectories. For example, the controller may receive a first proposed treatment trajectory 132, but may determine that the score for the first proposed treatment trajectory 132 is unacceptable. The controller can access the machine learning system and identify a second treatment trajectory 134 which improves the score to an acceptable level.

According to the example of FIGS. 2A-2D, the organ is a kidney. Kidneys function to filter blood that flows through the kidneys via the renal artery into a vasculature in which the renal artery branches into smaller and smaller blood vessels. The smallest blood vessels reach nephrons within the kidney, and the nephrons filter the blood and direct the filtered blood to corresponding veins. In determining the score for a proposed treatment trajectory 208 for a kidney, the machine learning system may determine the amount of the vasculature that is to be removed, taking into account any portion of the vasculature expected to regain function in the long term.

In some examples, the machine learning system may be trained to determine a percentage of nephrons that remain functional or active post-operatively. In this regard, the system may take into account the nephron density in regions of the kidney to be excised. For example, a kidney may have regions of high nephron density and regions of low nephron density. The density of nephrons may correspond to the vascular density, with active nephrons corresponding to density of capillaries or other blood vessels. Accounting for the density of nephrons can affect the score and associate the score with the post-operative functionality of the kidney.

During a procedure, blood flow may be temporarily disrupted to the organ, or at least a portion of the organ subject to a proposed treatment trajectory 208, to allow the practitioner to perform the procedure without excessive blood loss and to keep the region of surgery free from blood. If blood flow is disrupted for an extended period, the organ or the vasculature within the organ may develop ischemia. In this regard, the machine learning system can be trained to provide the practitioner with an estimate of the time for which blood flow may be safely disrupted. For example, the system may use the proposed treatment trajectory to identify regions most susceptible to ischemia and, using various factors, determine a safe length of time for disruption of blood flow. The various factors may include the region and size of the organ affected or the amount of blood flow adjacent to the affected region. Additional factors may include the age, gender, and health of the patient, as well as the health of the organ. The machine learning system may be trained to associate such factors, as well as historical medical data and other information provided by the user, with safe lengths of time for the disruption of blood flow.

Following a procedure, the practitioner must perform renorrhaphy to close an incision on the kidney. The suturing may be performed to minimize damage to the organ. In one example, suturing of the kidney may be performed in two layers including base-layer suturing and cortical renorrhaphy. In other examples, the practitioner may elect to perform base-layer suturing without cortical renorrhaphy. In other examples, the practitioner may elect to forego suturing in favor of a tissue adhesive such as bovine serum albumin-glutaraldehyde tissue sealant, which may result in less damage than suturing.

As noted above, in some examples, the machine learning system may be provided with multiple proposed treatment trajectories, for each of which the system may output a score. In some examples, the system can determine and provide to an estimated functionality of the organ remaining post-operatively. For example, the system may indicate to the user that the post-operative functionality of the organ is estimated at 75% for a first treatment trajectory 216 and 85% for a second treatment trajectory 218.

In some examples, the machine learning system may indicate to the user if a proposed treatment trajectory will impact a critical region of the organ. For example, the machine learning system may be trained to recognize regions of the organ that are associated with significant loss of functionality. Thus, if a proposed treatment trajectory will impact this region, the system may indicate to the user that this region should be avoided.

Further, the machine learning system may allow the controller to suggest treatment trajectories based on input from the user and/or the imaging system. In this regard, the machine learning system may be input with information (e.g., images) indicative of the portion of an organ to be excised. For example, the machine learning system may identify from images received from the imaging system regions of the organ that may be affected by a cancerous tumor 200. Alternatively, or in addition, the system may receive as an input from the user an identification of regions to be excised. The input from the user may be provided in the form of coordinates that identify the region or a graphical marking of the region to be removed.

The input from the user may include a minimum desired margin 220 within the region to be excised. Alternatively, the user input may include only the affected portion (e.g., cancerous tumor 200), and the user may separately indicate a desired margin 220. Similarly, when the machine learning system identifies the region to be excised based on information from the imaging system, the controller may add a margin 220. The margin may be based on certain guidelines or on input received from the user.

Once the region to be excised (including the margin) is identified, the machine learning system may identify the one or more available treatment trajectories 216, 218. In this regard, the machine learning system may also present to the user additional information associated with each proposed treatment trajectory 216, 218. For example, the system may output a score associated with each treatment trajectory 216, 218 and/or remaining post-operative functionality of the organ with each treatment trajectory 216, 218.

In other examples, the region to be excised (e.g., tumor 200) determined by the controller may not include a margin. In such cases, the user may provide the machine learning system with a minimum desired post-operative functionality. In these cases, the system may be trained to associate the input functionality with a treatment trajectory that maximizes the margin 220 around the region to be excised while providing the desired post-operative functionality of the organ. For example, along with indication of the region to be excised, the system may receive input from the user that 80% post-operative functionality is desired. The machine learning system, being trained to associate this information with potential trajectories, may then output the treatment trajectory 218 which provides 85% post-operative functionality while maximizing the margin 220 around the affected region 200. If the desired post-operative functionality is not achievable with any margin, the system can indicate to the user the maximum post-operative functionality available with zero or minimal margin.

In some cases, in identifying available treatment trajectories, the machine learning system may take into additional information, either based on input from the user or from the machine learning system. For example, as noted above, the machine learning system may identify critical regions of the organ which should be avoided by the treatment trajectory. Similarly, the user may provide input to avoid certain regions. The machine learning system may use such information as constraints in identifying available treatment trajectories.

As suggested above, the above machine learning system may be implemented on any of the controllers of the system 100, and may be implemented according to information association and analysis methods other than machine learning. As such, the above-described systems may be implemented as a non-transitory computer-readable storage medium, such as a memory device. In this regard, the non-transitory computer-readable storage medium is encoded with instructions executable by a processor of a computing system. For example, the instructions may cause the computing system to obtain an image of a patient's soft-tissue organ through an imaging device, receive at least one proposed treatment trajectory through a user input device, and generate a score related to a post-operative function of the organ for each of the at least one proposed treatment trajectory. Further, the outputs discussed herein (e.g., a score or proposed trajectory) may be provided to the user on a display device, such as HMI 112. Similarly, the systems can receive inputs from the user through HMI 112 or other input devices.

In addition to the training discussed herein, the machine learning systems in any of the discussed embodiments can be continually or iteratively trained. As such, the systems can continue to learn as they are used and can be exposed to more patients, procedures, and outcomes. Additionally, such training may be based on synthetic experiences that may be generated from simulations using modeled systems. In some examples, the machine learning systems can be trained with data comprising treatment trajectories and corresponding surgical outcomes of historical surgical treatments.

More generally, training a machine learning system with like physiological information of a tissue and various cuts (or other instrument actions such as excisions and reconstructions), the machine learning system can be trained to output a predicted result of the instrument action. This physiological information may be derived from anatomical models, imaging of the patient, and the like. Similarly, the system may be trained to accept a desired end result as an input and thus output an instrument action that achieves the result. Still further, the system may be trained to analyze potential risks and rewards for various actions and output recommend procedures. For example, the system may compare the risk associated with excising too much tissue (e.g., cutting farther from a tumor and thus further decreasing end organ function) with the risk of potentially leaving tumor tissue by cutting too close. Such system outputs may provide a recommendation to a user, or identify the relative risks and benefits associated with a plurality of cut lines (or other instrument movements).

Put another way, the machine learning system can be trained to analyze a virtual patient model and analyze the vessel structure of the patient, and then output estimated vessel structures correlated to organ function. The system may also analyze proposed cuts and determine the relative risks of violating the tumor by cutting too close, of compromising the procedure, and of the change in organ functionality based on a given cut. This analysis can be applied to a plurality of cuts, with the results of each cut presented to the user with estimations on each of the three risks, and/or a recommended cut. A user (e.g., a surgeon) can then weigh the tradeoffs and choose a final cut. Such a system can help improve patient outcomes by producing a reliable estimation of organ function based on cuts made on end arteries for a given patient.

Still further, the machine learning systems can anticipate and predict user decisions by recognizing common patterns. For example, the machine learning system can use data from past operations to make "trajectory suggestions" for the robot by recognizing common patterns of usage for certain movements and contexts. The system can also analyze a particular user's past or present use patterns in order to make predictions about what the user might want to do. Similarly, common errors may be recognized and automatically remedied. For example, where a pattern of movements suggests a result that may be harmful or otherwise undesirable, such an output of the machine learning system may trigger an alert or warning.

Still further, the trained machine learning system may provide feedback to users. For example, extracted information from a simulated or pre-planned surgical procedure, or from an actual prior procedure can input to the machine learning system. The system may thus be trained to output an evaluation of that procedure by associating an input procedure with known patient outcomes. Such outputs may include summary statistics useful in planning of patient care (time under anesthesia, expected blood loss, etc.) or material planning for the surgery (power consumption expected, total cost of materials, etc.). These summary statistics can be displayed in real time while the user is constructing a procedure. In addition, the system may agglomerate many summary statistics together into a single measure or score of surgical resource use. Other outputs can include an expected patient outcome and/or a suggested optimization of the procedure for that predictor. For example, if a total length of sutures predicted by the trained machine learning system negatively correlates with good patient outcomes in a particular context, the output of the system may suggest optimizing the procedure to reduce the number of necessary sutures. In yet another example, the output of the machine learning system may be an evaluation of user performance to verify user competence.

In still another example, a machine learning system can be trained to improve the actual movement of a surgical robot. Such a system may be integrated with, or informed by, the above-described simulation systems used for pre-surgical planning. For example, the systems can control movement of the surgical robot according to particular trajectories to effectuate the actions identified by the above-described pre-planning.

More particularly, control of electromechanical systems such as surgical robots depends on fine adjustment of the control parameters of the actuators of the robot. Analysis of past movement data and sensor data can be used with iterative learning of the machine learning system to automatically tune these parameters. Inputs to such a machine learnings system may include patient vital signs, current robot states, and the like; and outputs may include control signals to the robots and/or displays or like outputs identifying recommended movements to a user. Accordingly, the robot may be controlled according to the machine learning system in real time. Such a system may be integrated with the simulation systems described above, so that the surgical control system can adapt to expected circumstances rather than merely responding to circumstances as they are currently.

For example, if a patient's blood pressure rises, that input is recognized by the machine learning system, which is trained to output an alert (or otherwise recognize) that the material properties of the kidney will change. Further, the machine learning system may then output a signal that controls the robot to adjust force control gains to ensure that the correct amount of force is used to make an incision in the kidney. According to another example, the machine learning system may be input with information indicating that the patient is elderly and thus provide control outputs that are limit force and speed due to fragile tissues of the patient. In response, the robots can be made to slow down and use less force.

Still further, specific movements of a surgical robot may be optimized for given procedures. Due to limitations such as human error, suboptimal real time path planning, hesitation, and biomechanical constraints, robotic surgeries may include robot movements that serve no surgical purpose or are otherwise inefficient. Accordingly, machine learning systems that improve control of surgical robots may be trained to do so by optimizing movements of the robot. In one example, such optimization is performed by detecting and removing non-purposeful movements. Such movements may be determined based on a conceptual simplification and assumption that any movement that results in a change in the physical contact state between a surgical instrument and the patient is a purposeful movement. For example, the movement of a scalpel cut is functional only while the scalpel blade is physically touching tissue. Suturing movements only "do" something while the needle drivers are actively touching the needle or thread.

Figure 3:
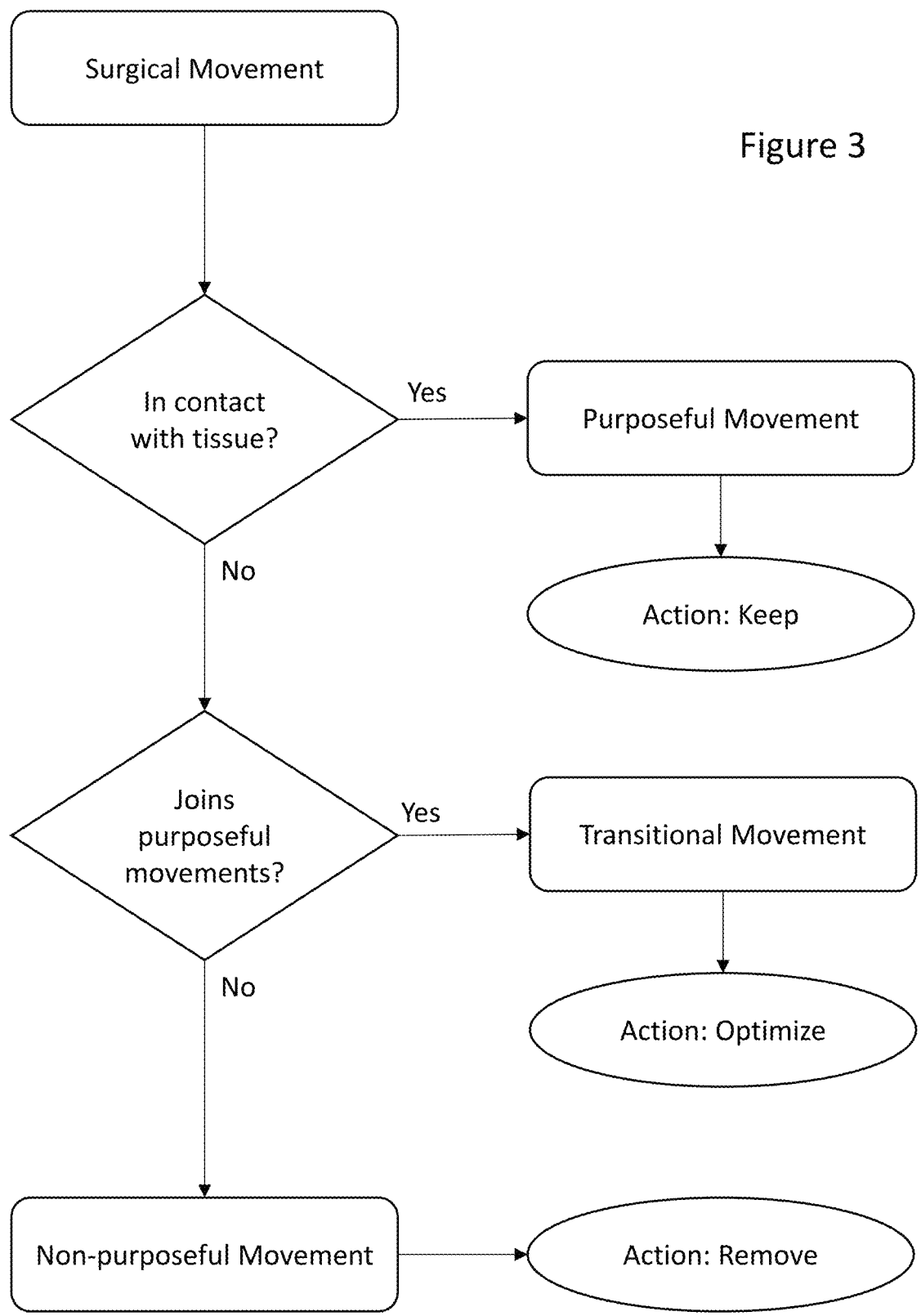
FIG. 3 illustrates a method for optimizing surgical robot movements.

Based on these assumptions, movements executed by the surgical robot may be optimized according to the method of FIG. 3. More particularly, surgical movements where touching begins, occurs, or ends have a high chance of being functional and thus are categorized as "purposeful movements". These movements remain unmodified. Outside of the above functional movements, all other movements merely serve the purpose of transporting the surgical instrument between active sites where touching happens, and thus are ripe for optimization. Such movements are categorized as "transitional movements". The transitional movements may be optimized by using common motion planning algorithms based on layers of simple rules. For example, one optimum path may be a straight line path between the last touch and the next touch. Another rule that may be applied to the optimized movement may be to not collide with anything when moving. Similar other rules may be utilized to optimize any path of these transitional movements. If a particular movement does not end or start physical contact, it is identified as a "non-purposeful movement," and can be eliminated (or alternatively, converted/merged into an optimized "transition movement"). Finally, periods where there is no movement at all may also be removed. This approach may be applied to any set of surgical movements, for example, while planning for and optimizing a robotic surgical procedure.

As the above disclosure for optimizing surgical robot movements can rely in part on detecting/identifying purposeful movements, another aspect of the present disclosure relates to systems and methods for detecting touch of an instrument of a surgical robot, particularly on a patient tissue. There are a variety of sensing methods that can be fused to reliably sense touch. For example, force sensing may be applied, but force by itself is limited because it cannot easily distinguish between different materials, and it struggles to detect materials that are soft or liquid. Likewise, imaging or optical solutions can be employed, but they are limited because of their inability to deal with occlusion.

Figure 4:
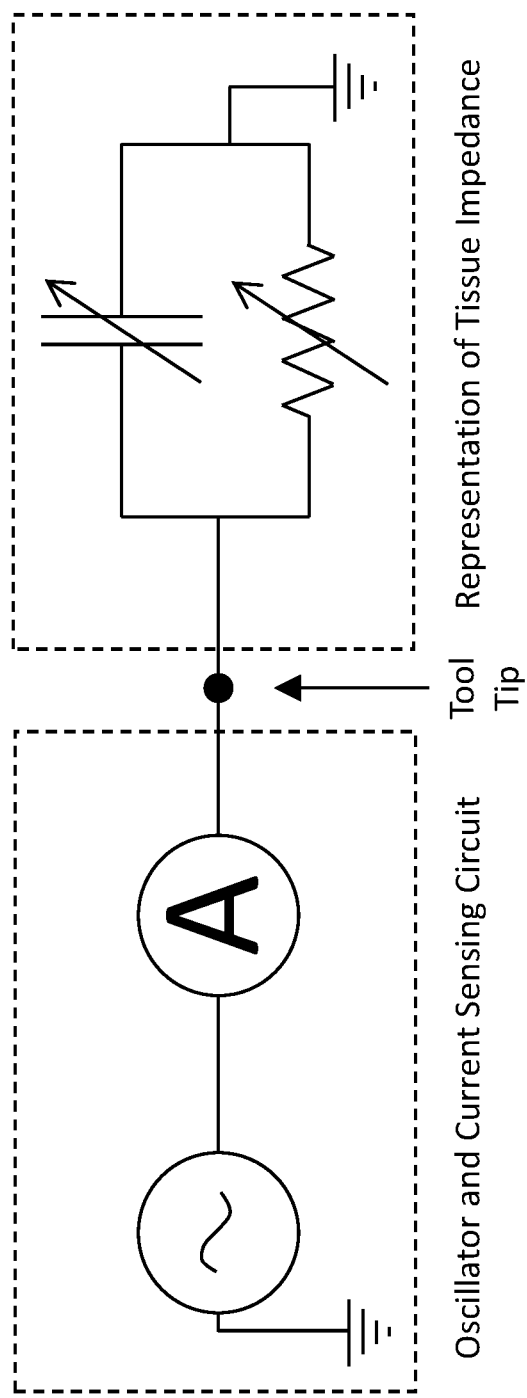
FIG. 4 is a schematic representation of the capacitive detection of touch with surgical instruments.

However, capacitive touch sensors can detect the magnitude and position of a capacitance change as measured by an oscillator when a conductive object enters the electric field of a capacitor driven by that oscillator. Using this technique can distinguish between a human finger and metallic or nonconductive objects based on the characteristic impedance these objects present to the oscillator. A similar principle can be applied to surgical instruments, as schematically illustrated in FIG. 4. As seen therein, an oscillating electric field is applied to the tip of a surgical instrument, and physical contact of that instrument with a conductive surface can be detected based on the load the surface presents to the oscillator producing that electric field. Because the magnitude of the loading depends on the impedance of the material touched, it is possible to differentiate between different materials based on a measured impedance. This can either be a measure of conductivity (if touching conductive objects) or a measure of permittivity (if touching insulators). Such a system is operable with voltages and currents that are of a safe magnitude for use in surgical procedures, and that avoid Ohmic heating, arcing, or cardiac disturbances. In addition, efficiency and sensitivity of touch detection for specific materials may be further improved based on the frequency of the oscillator, which may be adjusted based on a desired surgical context.

When touch is detected, systems and methods of the present disclosure may further provide haptic feedback to the user. Without such haptic (or like) feedback, it is impossible for a surgeon to know if accidental contact has been made if it is not apparent in a teleoperative visual field of view. However, with touch information directly obtained from the robotic end effectors, it becomes possible to provide haptic (or like) feedback to the surgeon directly proportional to the touch sensed by the end-effectors. In addition or alternatively to the haptic feedback, the feedback may be audible, visual, or the like, which can also provide the surgeon with relevant information regarding interaction of end-effectors with other objects (such as tissue). For example, a sound intensity may be proportional to the touch pressure sensed by an end-effector. In another example, an object displayed on a screen (e.g., a box) may change size, shape, color, brightness, or the like, corresponding to a level and type of touch sensed by the end-effectors.

Another aspect of the present disclosure relates to sensors for measuring time-varying changes in the position, orientation, and shape of instruments (or other objects) being manipulated during a procedure. Position information is currently obtained by surgeon visualization via a camera and/or pre-operative imaging data providing context.

Positions of instruments or other objects attached to the end of a surgical robot arm may be estimated based on positional knowledge of the robot itself (e.g., from internal sensors of the robot). However, these estimates become less precise for less rigid objects. It is in this continuum of deformability that spatial tracking of all elements (anatomy and tools) becomes more difficult.

One approach to 3D tracking of deformable objects (instruments, objects, tissues, and the like) for surgical navigation includes a system having spatial tracking sensors, a mesh to hold the sensors in a known relationship to an object of interest, and a corresponding processor configured to perform the real-time registration of the object to a known reference frame for the surgical system. The sensors can be based on any 3D spatial tracking techniques including optical, magnetic, thermal, radio-frequency (RF), ultrasonic, radioactive, and the like. Further, the sensors may be arranged on the mesh in an arbitrary pattern or pattern other than an array in or across multiple regions of a single mesh. Such variations may be desirable where spatial tracking is more difficult or more desirable at one location that another.

For example, optical sensors may determine position with a stereo-camera system, where the position of the camera is in a known reference frame relative to the surgical system, and it detects passive reflective light from a sensor, detects passive fluorescent light from a sensor covered with fluorescent dyes or proteins, detects active light (e.g. LED) from a sensor; and/or utilizes a variety of image processing algorithms (including machine learning and AI) to locate a point of interest in 3D space from video data. Similarly, thermal sensors can determine spatial position by a stereo-thermal camera system, where the position of the camera is in a known reference frame relative to the surgical system, and elevated temperature heat emitters are located in the field of view of the cameras. Magnetic sensors can sense spatial position where the position of the magnetic field emitters are in a known reference frame relative to the surgical system, and the individual sensors use the magnetic field strength to determine their location.

RF field spatial sensors can determine position by utilizing RF emitters in a known reference frame relative to the surgical system, and an RF receiver to sense the strengths, phases, and the like of signals emitted from the individual RF emitters. Similarly, ultrasonic sensors can be used to determine position with a stereo-ultrasound system, where the position of the detector is in a known reference frame relative to the surgical system, and the individual markers emit signals that allow the detector to determine their location based on their strength, phase, and the like. And radioactive beads can be used to determine spatial position with stereo-radioactive detector system, where the position of the detector is in a known reference frame relative to the surgical system, and the individual radioactive markers emit low dose radiation detected by the detector.

With reference to FIGS. 2E and 2F, the individual sensors 222 may be embedded in a grid-like mesh (e.g., to hold the sensors in an array) 224 that can be attached to the organ (e.g., kidney in FIGS. 2C and 2D), surgical tools, or other anatomical items of interest. Accordingly, the mesh 224 holds the sensors 222 on the surface of the object (e.g., an organ or other patient tissue) being tracked. Although the sensors 222 may be generally affixed to the mesh 224 in a grid or array, the density of sensors does not need to be constant across the entire mesh. Rather, one region of the mesh may have a greater density of sensors than another region.

In one example, attachment of the mesh to the patient can be in the form of a bag that wraps around and is cinched in place to track an organ such as the kidney. The mesh also can be in a form where it attaches directly to tissue with a micro-barbed surface. The relative relationship between the sensors does not need to be maintained by the mesh. Rather, the mesh fibers can be stiff or elastic along their length, or otherwise deformable in two or three dimensions. In other forms, the mesh may include expandable elements (e.g., such as with an expandable stent that takes size of lumen) so that it may be placed in a vessel, or have a C-shaped design and be placed on the outside of a vessel with nitinol rings used to wrap and retain grip on vessel. The mesh can also be made bioabsorbable and/or biodegradable, so that fibers can be left in the body following the surgery. If the individual sensors are passive (e.g., do not have wires attached) then the mesh can be cut to fit the anatomy. If the sensors have wires, or the mesh otherwise cannot be cut, individual smaller-sized meshes can be patched to cover a desired area.

So that key anatomy and patient specific geometry of the object being tracked (e.g., an organ) is known a priori, anatomical imaging (e.g., MM, CT) data can be pre-processed into a 3D model. Real-time positions for each sensor of the mesh as determined by a processor based on signals from corresponding detector(s) can then be registered with the 3D model. This registration can be based on best fit techniques to establish an estimate of the location of the organ, surgical tools, or other items of interest in the known reference frame of the surgical system. Additionally or alternatively, registration of the sensor data may be made to real time intraoperative (rather than pre-operative or like a priori) images.

In one embodiment, the above-described sensors and mesh can be used for surgical navigation and tracking. Example navigational uses include a mesh bag around the kidney, where registered sensor positions or used to generate a grid to locate relevant anatomical structures relative to surgical tools. This registration can be used to aid a surgeon cutting around a tumor. The mesh may also or alternatively be used as an overlay for locating the tumor. In still other examples, the mesh and sensors may be used for rectal or prostate surgery. Example tracking uses include a mesh used to track deformation of a tissue, for example, as an instrument (e.g., a scalpel) interacts with the tissue as described in more detail below.

Considering the above, still another aspect of the present disclosure relates to control of robotic systems during interaction with deformable bodies or rigid bodies. Deformable bodies may be the instrument (connected to the end effector of the robot) used by the robot, or the stationary body on which the robot works (e.g., a patient organ). The interaction between the robot/instrument and deformable body can be represented by a model and/or monitored in real time for example through the use of the above-described mesh. In one example, the model creates a virtual ancillary sensor at the location on or within the deformable body that is closest to the part of the instrument that will be in contact with the tissue. If the instrument is not actually in contact with the body, then the model will output the projected nearest body position.

This model may be an approximated constitutive model based on preoperative imaging data, material properties such as elastic modulus and strain, force, position, constitutive parameters, the initial morphology of the deformable body (e.g., its rest shape), sensor data, and other parameters. The rest shape can be a common rest shape derived from any simulation, 3D printed surgery planning, and the actual procedure. Using a common rest shape allows for space warping between the surgical planning and the robot control. In order to perform space warping, the model is interrogated to get: 1) a virtual 6D ancillary sensor position of the nearest point on the deformable body relative to the tool, 2) the same virtual 6D ancillary sensor position for the rest shape of the deformable body, and 3) the relevant forces in the deformable body coordinate system or as transformed to the virtual ancillary sensor position.

Obtaining the parameters described above allows for space warping of an initial trajectory of an instrument relative to a deformable body due to deformation. A robotic trajectory created for a deformable body uses a deformable body reference shape. Depending on the embodiment, the reference shape may be the rest shape. This trajectory specifies the position control pose (PCP) between the robot instrument coordinate system and the reference deformable body shape, considering the instrument is typically at the end of a robot. The body is either stationary or can move relative to a fixed coordinate system.

Space warping relies on the model output to continuously move the reference deformable body shape utilized by the trajectory to the location that provides the best estimate of where it would be after the deformable body has changed shape. An example of this concept is illustrated in FIGS. 5A and 5B, where a robot 500 is programmed to draw a line on top of a board 502 with an instrument 504. In the scenario shown in FIG. 5A, the board 502 has three supports 506 across its axial length, so it does not deform or deflect as the robot 500 moves along the axial direction. The robot 500 is programmed purely in position control and moves along the axial direction of the board 502 and maintains its position in all other degrees-of-freedom. However, in the scenario of FIG. 5B, the board 502 is only supported by two supports 504 on one half of its length. Without the ability to warp space, the instrument 504 would move to the right with no knowledge of the curved surface of the board 502. After the instrument passes over the second support 806 from the left, it would stop touching the board 502 and would be unable to perform its task. With space warping, however, the board's reference shape would be projected to the location on the board closest to the robot instrument 504. Thus, as shown in FIG. 5B, the instrument can follow the surface of the deformed board 502 tipping up on the left side and down on the right side. The instrument 504 is able to follow the board's surface because it is constantly moving the reference shape to the current instrument position and using the reference shape's coordinate system to define the position control pose. In other words, the instrument takes on the reference shape's coordinate system so that the movement of the instrument matches that of the deformation. This reference shape is shown in FIG. 5B overlaid on the original body. Accordingly, the trajectory from FIG. 5A may be used to perform the task in the scenario of FIG. 5B.

Figure 6A:
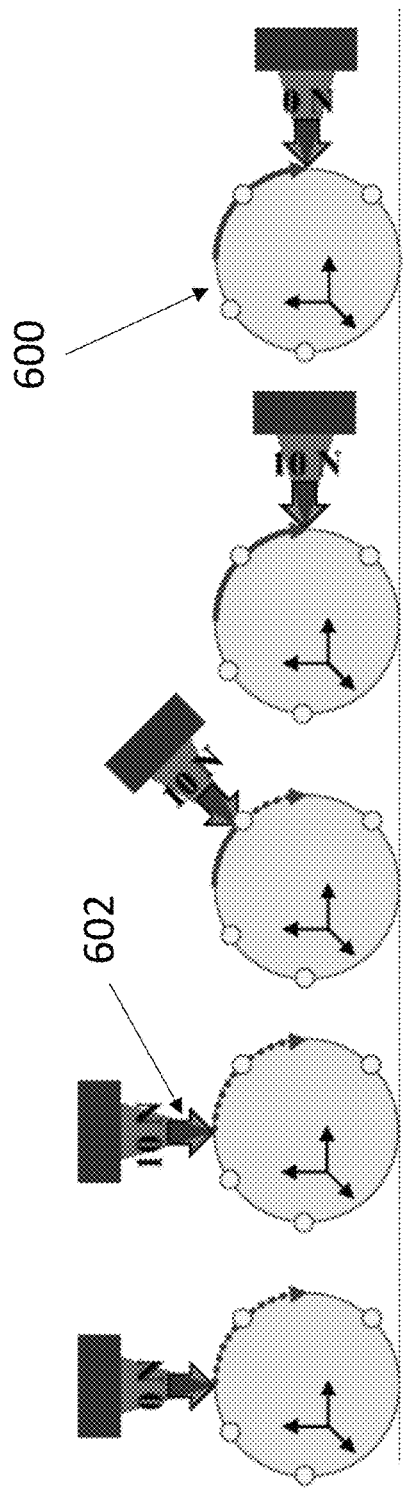
FIGS. 6A and 6B illustrate a second example effect of deformable bodies on robot trajectory.
Figure 6B:
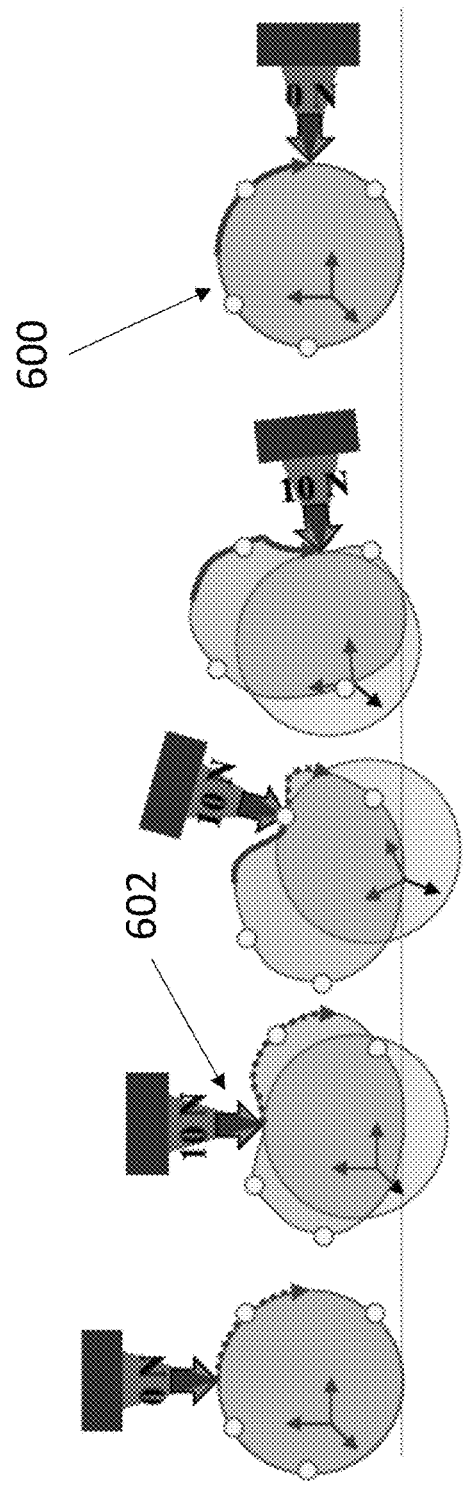

A second example based on a kidney 600 and suturing instrument (e.g., a needle) 602 is illustrated in FIGS. 6A and 6B. As seen in FIG. 6A, treating the kidney 600 as a rigid body allows the instrument 602 to simply move around the perimeter of the kidney 600 according to its known shape. However, as shown in FIG. 6B, because the kidney 600 is actually a deformable body, as soon as the instrument 602 comes in contact with the kidney 600, the kidney 600 changes shape due to the force (e.g., 10 N) applied. Without space warping, the programmed trajectory of the instrument 602 would execute an incorrect series of moves because it will be operating under the assumption that the kidney is always the same shape (as in FIG. 6A). Space warping, however, allows the instrument 602 to follow the initial trajectory made relative to the reference shape even as the kidney changes shape in real time. As above, FIG. 6B shows the kidney reference shape overlaid to show how it is used to map the PCP used in the trajectory to the deformed shape of the kidney.

It is noted that the kidney in FIG. 6B is assumed to be a completely elastic material, such that it returns to its original shape after the external force is removed. If the body is not elastic, then it would not go back to the initial shape. For accurate repeatability and/or determinism in robotics with deformable objects it can be preferred to have more information than just the PCP to execute a trajectory. While a position control pose between these two rigid bodies completely describes their spatial relationship, when space warping is introduced to account for deformation of the instrument or other body, a position control pose can have infinite solutions. For example, FIGS. 6A and 6B can describe the same position control pose. However, as a function of material properties or contact force, the deformable body can deform in many different ways. This is desired behavior of the position control pose when trying to put the instrument tip at a specific location on the object in the presence of deformation. However, it means that for a given position control pose, there is not a unique solution for where the instrument should be. In turn, this means that in order to have deterministic playback of the instrument's motion relative to the deformable body, the position control pose alone may not be enough, and other process variables may be needed. Such variables may include the forces exerted by the instrument on the body, and/or the absolute position of the instrument relative to the body (an absolute position control pose).

These process variables allow robots to correctly execute what was intended during a planning or simulation of a procedure. For deterministic playback to work in the presence of deformable objects, the position control pose and forces should be replicated, or the absolute position control pose should be replicated. Differences between deformations in vivo, in vitro, and in silico, may be present because of error in modeling and/or material property differences with each modality. Therefore, when transitioning from a simulation or test to an actual procedure, the position control pose forces may be played back to get a similar mechanical response out of the system. Thus, a unique control scheme for the position control pose may utilize hybrid force/position control in several degrees-of-freedom when programming trajectories in one modality (typically in silico), and executing it in another. Incorporating force yields an unambiguous relationship and unique position control pose.

If force control is not available or the robotic process is sufficiently repeatable (perhaps due to extremely repeatable deformable body behavior), then the absolute position of the instrument relative to the body may be played back (i.e., the position without space warping). Absolute position playback is equivalent to the concept of superposition testing. Absolute position control pose may not work sufficiently when running a trajectory in one modality and then switching to another modality. However, using absolute position control pose can provide sufficient results when repeating procedures within the same modality (e.g., in vivo).

In short, there is desire to program a robot to execute a trajectory on a deformable body in real time as the deformable body deforms, to execute the same trajectory on a deformable body in silico, in vivo, and in vitro, and/or to execute the same trajectory accurately on a deformable body whose behavior is not repeatable. The above-described techniques address these concepts.

Additionally, imaging technology can be utilized to compensate in real time for tissue deformation, by automatically synching image recognition capabilities of different imaging modalities and surgical robots. More particularly, multiple imaging modalities can be synchronized with each other to form hybrid images. Real time images can be collected using various modalities such as ultrasound, doppler, elastography, biometric impedance, fluorescence imaging, thermal imaging, laser imaging, and the like. High definition coaxial imaging can be collected from devices like MRI, CT, PET scan, and the like. Digital tags can be used to mark anatomical features on the coaxial image such as the center of a tumor in a prostate. Sensor data (e.g., from the above-described mesh) may also be registered to the images. When the intraoperative real-time images are collected, the data from the different modalities can be overlaid to locate the anatomical feature defined by the digital tag in real-time. In other words, the images from multiple modalities can be registered to each other based on the digital tags of anatomical features, and further registered to real time sensor data collected from a mesh.

In the case of deformable objects, registration permits the pre-operative coaxial image to take on the deformed shape of the object imaged by the intraoperative real-time images and visualized in the hybrid image. In this way, even though the pre-operative coaxial medical images are taken before the procedure and thus do not represent any deformed anatomy, they can still be utilized to visualize deformed anatomy caused by cutting (including excising or reconstructing tissue), handling, and otherwise pushing of the patient's tissues once a procedure starts. As a result, the hybrid images are more accurate and compensate for tissue deformation in real-time. An example method for achieving this end is illustrated in FIG. 7.

Figure 7:
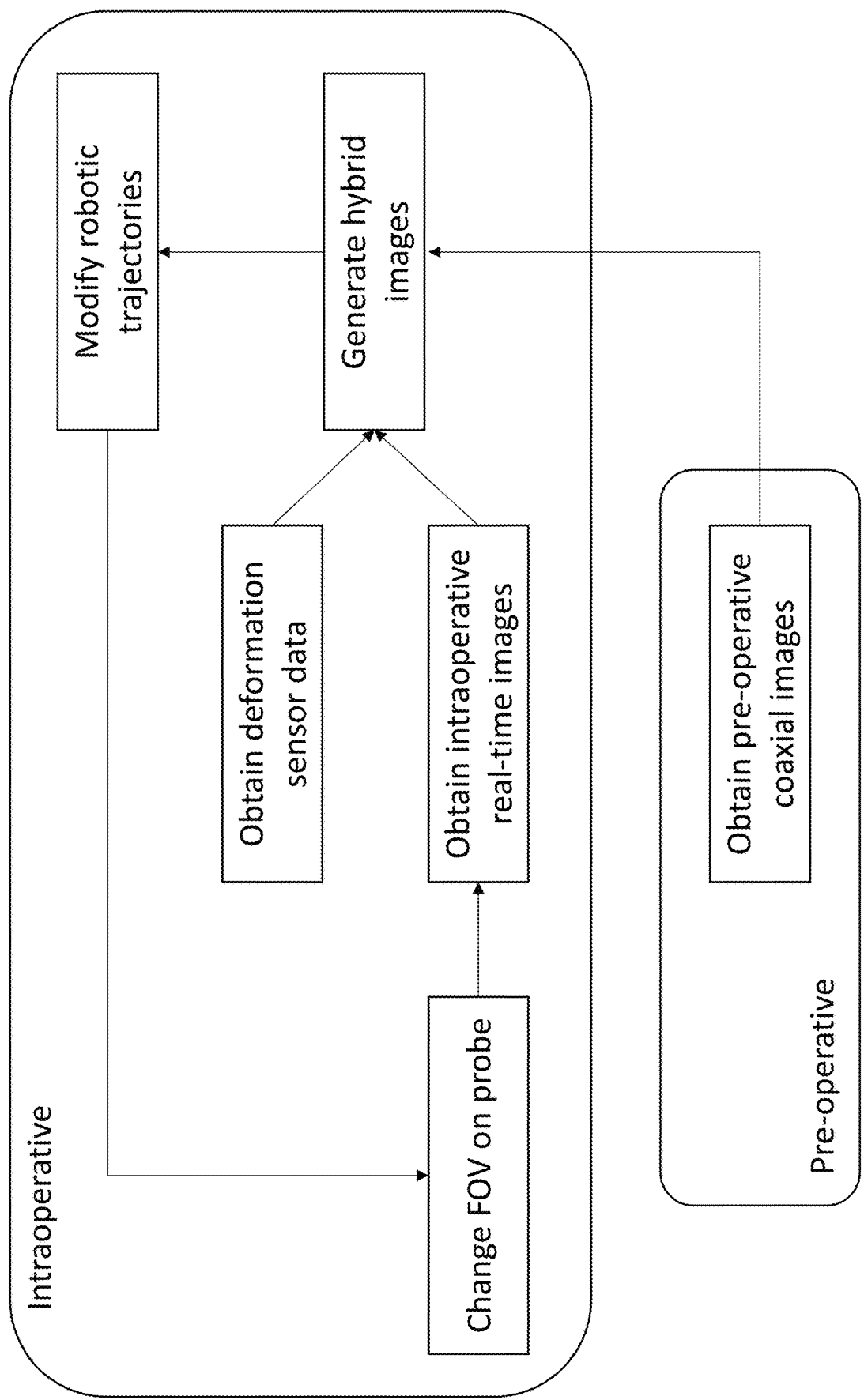
FIG. 7 is a flow diagram illustrating a method for synchronizing imaging to control surgical robots for real-time compensation of deformable bodies.

According to the example of FIG. 7, prior to executing a procedure (e.g., a robotic prostatectomy), a pre-operative coaxial image such as an MRI is taken of the operative tissues (e.g., in and around a patient's prostate). The surgeon then defines a digital tag at the center of the tumor in the prostate in the MRI image. During the procedure, an ultrasound probe (e.g., inserted into the rectum) collects real-time images of the tissue in different fields of view (FOV). The intraoperative real-time images are combined with the pre-operative MRI images and sensor data (e.g., from the above-described meshes 210) indicating any deformations to highlight the digitally tagged anatomical features. The surgery can then be completed with a teleoperated robot having its trajectories modified automatically and in real time based on the hybrid images as a reference (as described above). Such increased accuracy and improved control of the robot helps the surgeon avoid vital structures like the nerves in a prostatectomy.

In some embodiments the above analysis can be performed with a trained machine learning system. For example, such a system may be trained to output the hybrid image based on input co-axial and real-time images, sensor data (e.g., from the above-described meshes 210), and the like. Additionally or alternatively, the machine learning system may be trained to output control signals to the robot according to a trajectory plan for the robot to perform a particular action based on a hybrid image, digital markers, and like inputs that avoid boundaries of important anatomical structures.

The above-described method can be implemented according to various system configurations. In one example, a passive ultrasound (or other real-time imaging) probe may be affixed to a stand inserted into the rectum (or other object being imaged). The ultrasound probe and the robots may be synchronized via a central controller, such as the coordinator 102. In another configuration, the main robot may include an additional arm that is fitted with the intraoperative real time medical imaging device (or like probe). Adding the dynamic element to the real time imaging probe can increase the procedure's efficiency by allowing the controller to adjust the probe to produce the best field of view to execute any part of the procedure at any given time. The other arms of the robot can receive commands from the central controller and compensate the field of view the probe produced to take into account the deformation of tissues seen in the procedure. And according to a third example, the central controller can command an additional robotics system. In other words, one robot can control the intraoperative real-time medical imaging device and transmit data back to the central controller, while a separate robotic system can control the procedure.

In a robotic partial nephrectomy example, a tumor or lesion is excised from the kidney while the kidney's good tissues are preserved. In this example, fat around the kidney can be dissected to have visual contact with the kidney's surface and, in some cases, the tumor or lesion's surface within the kidney. This can give easy access for a sensor mesh to be placed into the patient to track the deformation seen on the surfaces. In this example, the visible boundaries of the tumor are well defined within the view of a primary robot scope, which can be used for real time imaging and to generate the hybrid image. This scope may add a layer of redundancy and provide additional accuracy to the hybrid image.

The primary robot could also be affixed with an additional arm controlling an intraoperative real time medical imaging device that would be positioned on the surface of the kidney. This robot could automatically center the field of view, scroll, and be able to zoom in and out to optimize the image with respect to the tumor. The additional arm then can utilize the pre-operative coaxial images, intraoperative real time images, and tissues deformation sensor data to produce the hybrid image. The key anatomical features in the hybrid image can be defined and used to guide the procedure and/or utilized as feedback to optimize the field of view of the additional arm of the robot controlling the intraoperative real-time images.

Similar to above, one or more additional robots could be controlled by a central controller such as the coordinator 102, with the intraoperative real time medical imaging probe be affixed to a second robot. Again this system can be synchronized through the central controller to utilize pre-operative coaxial images, intraoperative real-time images, and tissues deformation sensor data to produce a hybrid image that be used to generate trajectory controls in real time for all the robots in the system. The robot that has the intraoperative real time medical imaging probe can optimize its view by translating, zooming and rotating to produce the best field of view for the procedure at any given moment.

Further, as discussed above, a resulting organ function may be predicted and scored based on a given procedure. For example, the excision of a tumor may be predicted to reduce kidney function by 25% given the desired trajectory plan to remove the tumor. Such information may also be utilized by a controller or trained machine learning system of the robot to control the robot trajectories in real time or refine trajectory plans prior to the procedure. For example, a machine learning system may also identify that a different trajectory plan to remove the tumor would only reduce kidney function by 20%, and thus adjust the trajectory plan of the robot to the less destructive plan.

Figure 8:
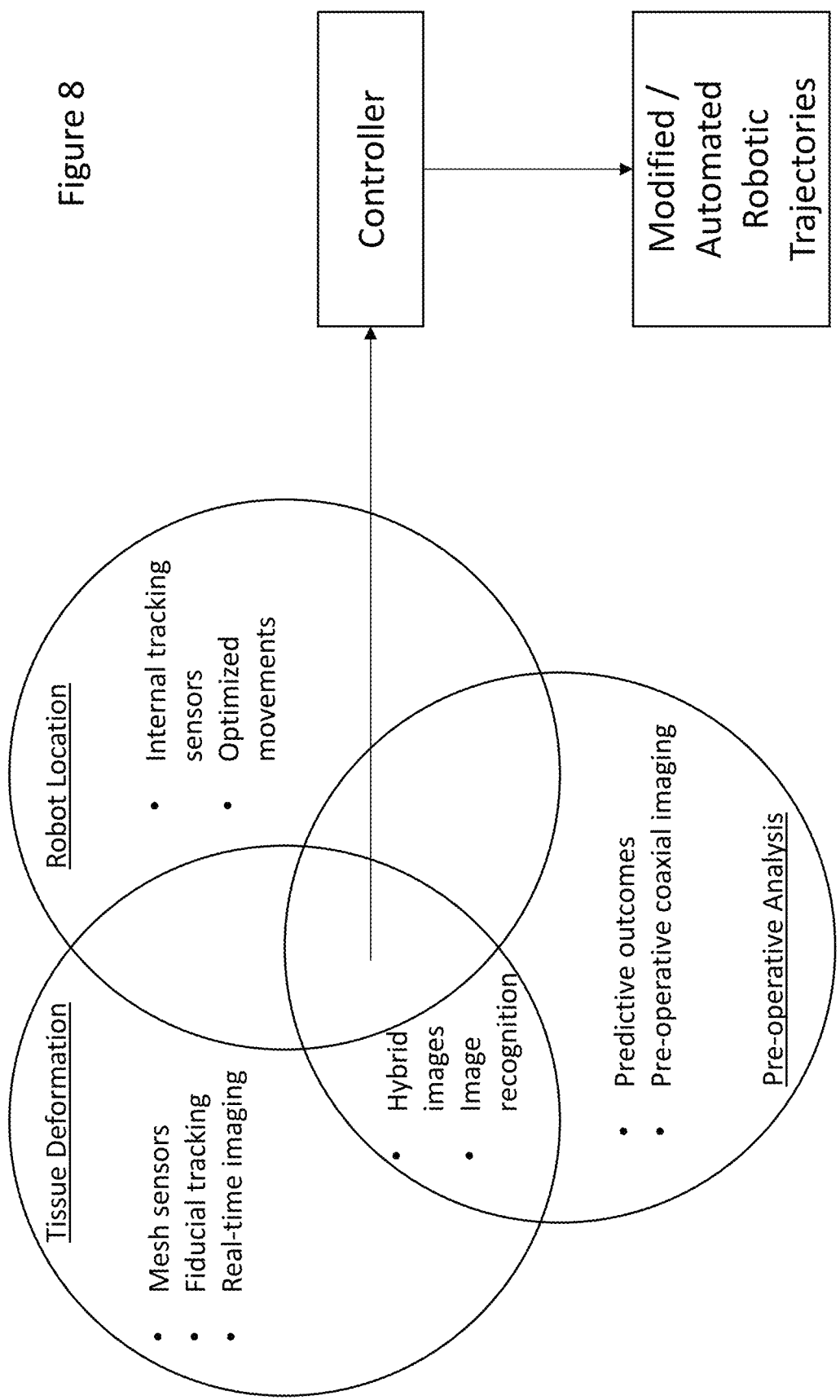
FIG. 8 illustrates the wholistic information used for controlling robot movements.

With reference to FIG. 8, control of surgical robots may be based on wholistic real-time information—that is, at least information related to tissue deformation (e.g., based on models and/or real time tracking with a mesh) and current positioning of the robot combined with pre-operative information and analysis (e.g., for generating hybrid images and/or predicting procedure outcomes) of the patient (and organ) on which a procedure is performed—to optimize and improve robotic movements during the procedure, and to improve outcomes. In other words, a controller or trained machine learning system of the robot may rely on the pre-operative images, intraoperative images, hybrid images, and/or sensor data (e.g., from a mesh) to determine deformation and future organ function for a given trajectory of the robot during the surgery. All or any portion of this information may then be used to control trajectories of the robot in real time to perform and optimize the procedure.

Another aspect of the present disclosure relates to the precision and control of robots manipulating objects in space. Generally, the position and orientation of an object in space can be described as a six degree-of-freedom (DOF) relationship involving three translations (x, y, z) and three rotations about those axes. Most robots use six motors and linkages between the motors to allow the robot to place the object at the end of the robot (e.g., the instrument) in this 6-DOF space. For a 6-DOF robot there is commonly only one pose (rotation angle or orientation of each of the six motors) that can place an object held by the robot at a desired position and orientation in space.

Another class of robot has seven degrees-of-freedom, where the seventh degree is a redundant axis. Redundant serial arm robots are capable of motions categorized as "self-motions" or "elbow swivels" in which the pose of the robot may change without effecting the end-effector position. For a 7-DOF robot, the redundant axis provides an infinite number of possible poses for a given end effector position (as defined in 6-DOF). With such robots, the pose can be modified to avoid joint limits (motor angles at the top and bottom of their range), singularities (poses where motor rotation axes are aligned and the mathematical control of the tool 6-DOF becomes ambiguous), and collisions (e.g., while placing the tool at a specific position and orientation in space, the rest of the robot arm may run into surrounding structures or moving objects, such as other robots or surgical equipment, medical personnel, regions of the patient not intended to be operated on, and the like).

The decision of what motor angle command to send to this redundant axis is typically left up to a robot programmer, a priori, through trial and error. However, according to the present disclosure, the redundant axis may be controlled automatically without a priori knowledge of where the object held by the robot is supposed to be.

Briefly, an example method for controlling the redundant axis calculates a velocity that, when applied to the redundant axis of a 7-DOF serial arm robot, drives the robot away from singularities, joint limits, and designated spatial collision points while maintaining a constant end-effector position. Given current axis positions and a list of points in space that should be avoided, this method of control is able to calculate a redundant axis velocity that will drive the robot to an optimal pose. More particularly, the robot's current state of redundancy can be represented by an "arm angle" that ranges between −180° to +180°. This arm angle exists on a circle (hereinafter a "redundancy circle") that lies on a reference plane (hereinafter an "arm angle plane") that contains all possible locations for the manipulator elbow given the current end-effector Cartesian position. The position of the manipulator elbow when the redundant axis is at 0 degrees is the reference position for the origin of the redundancy circle. Movement of the redundant axis while maintaining the end-effector position will result in movement of the elbow around the redundancy circle on the arm angle plane. The angle between the elbow at any given redundant axis angle and the 0 degree elbow position is referred to as the arm angle.

As suggested above, there are three possible hazards in movement of a robotic arm that should be avoided: collisions, singularities, and joint limits. First regarding collision avoidance, it can be difficult to define which side of a boundary is forbidden to avoid collision due to ambiguity in defining the robot's pose as a function of the Cartesian end-effector position. In other words, it can be difficult to determine an appropriate polarity to the determined collision avoidance velocity. However, this ambiguity can be resolved by applying a logical test to the algorithm output. That is, given a pair of boundary arm angles A and B on the redundancy circle, there are 3 possible zones: Zone 1: The zone defined by A-B; Zone 2: The zone defined by −180° to A; and Zone 3: The zone defined by B to +180°. Because the current arm angle of the robot is known, and it is known that the robot cannot exist in forbidden zones, the appropriate polarity can be identified. For example, if the robot is in Zone 2 or Zone 3, Zone 1 is forbidden; and if the robot is in Zone 1, then Zones 2 and 3 are forbidden.

For singularity and joint limit hazards, zones created from the joint limits for each joint are intersected with the zones mapped from singularities in order to create a single set of zones. While existing functions used for avoidance of joint limits can be effective, the singularity avoidance methods are not satisfactory when used in conjunction with the joint limit avoidance functions. Instead, a replacement function is described below. The general form of the singularity avoidance function used in this method of robot control is given as:

$$\Delta = \frac{x - buff_{sing}}{r_{sing}(x - buff_{sing})^2} - tol_{sing}$$

where $\Delta$ is the output of the function expressed as a change in arm angle of the robot, x is a current arm angle of the robot, $buff_{sing}$ is a buffer around the singularity that modulates the reach of the avoidance effect of the function, $r_{sing}$ is a reaction coefficient that drives the curvature (and hence the avoidance strength) of the function, and $tol_{sing}$ is a threshold for a dead band where the singularity has no effect on avoidance effort. Increasing the value of the buffer will cause the robot to react more aggressively further away from the singularity, increasing the value of the reaction coefficient will cause a stronger avoidance effort, and increasing the threshold increases the size of the dead band.

The singularity avoidance function is asymptotic at its edges to ensure that the robot does not wander into forbidden arm angle zones. However, for a collision avoidance function, the reaction cannot be asymptotic because the hazard is a physical object (or objects), which may move towards (or away from) the robot. An asymptotic reaction results in intense avoidance reactions when near boundary conditions. Due to this problem, a softer function is described below.

Figure 9:
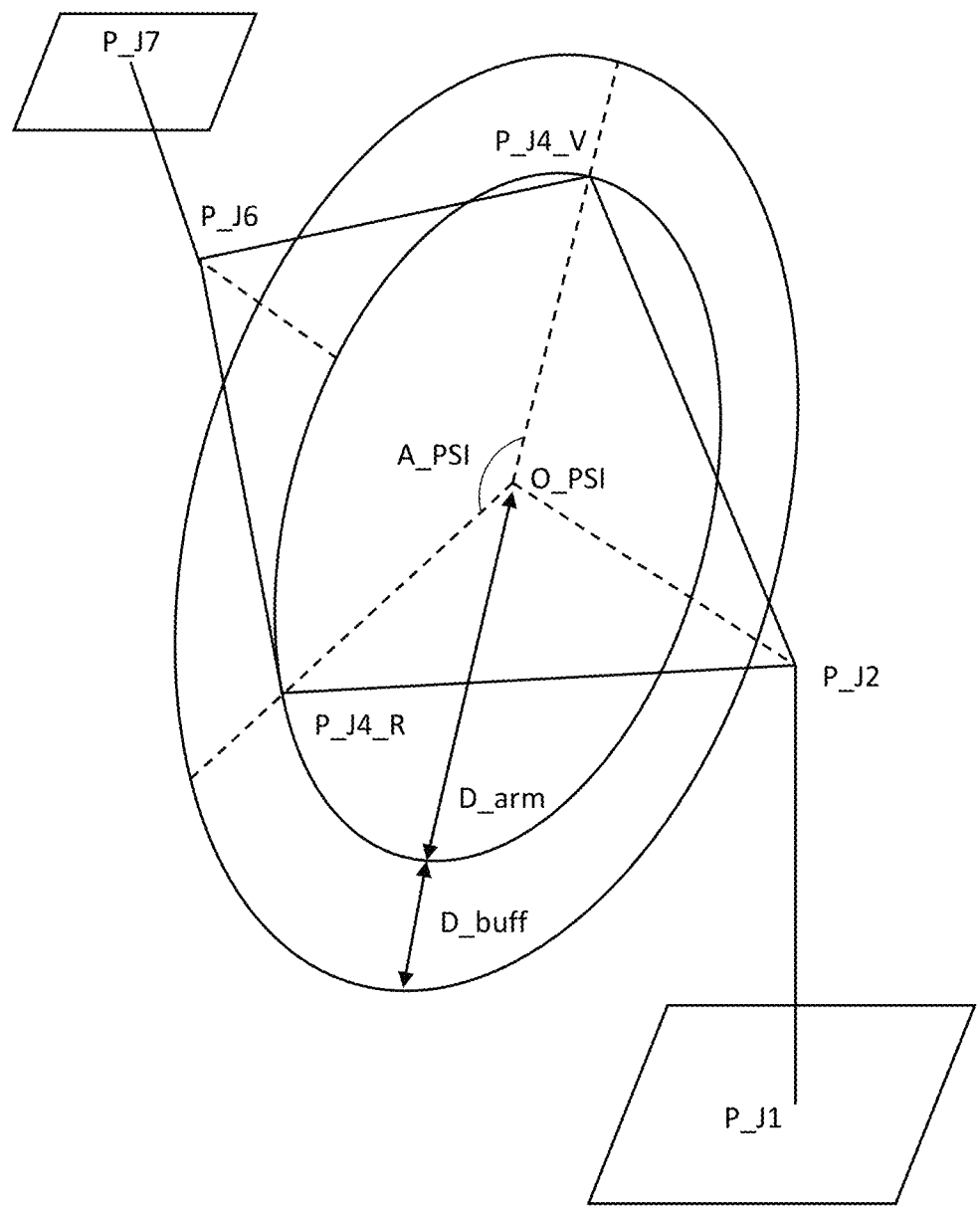
FIG. 9 is an illustration of the projection of a 3-dimensional position of an object in an external reference frame to a 2-dimensional robotic arm angle plane in the robot's reference frame.

In order to avoid an object (or anatomical region that should not be touched by the instrument held by the robot), the potential for collision with the object can be mapped to the redundancy circle. With reference to FIG. 9, this is accomplished by projecting the 3-dimensional position of the object in an external reference frame ("World 1") to the 2-dimensional arm angle plane which is defined in the robot's reference frame ("World 2"). Although in principle any axis of a redundant manipulator may be defined as the redundant axis, in this example Joint 3 of the robot is the redundant axis. In this arrangement, self-movement of the robot only results in a change in position of Joint 4 (the "elbow") to avoid collisions. The variables in the illustration of FIG. 9 are defined according to Table 1, below:

TABLE 1

Variables of FIG. 9

| Variable | Meaning |
| --- | --- |
| $P_{J1}$, $P_{J2}$, $P_{J6}$, and $P_{J7}$ | Positions of joints 1, 2, 6, and 7 transformed to the World 1 coordinate system |
| $P_{J4,R}$ | World 1 position of the real robot joint J4 |
| $P_{J4,V}$ | World 1 position of the virtual robot joint J4 (when joint J3 = 0°) |
| $O_{PSI}$ | Arm angle orientation |
| $\overrightarrow{P_{J2}P_{J6}}$ | Vector from joint J2 position to joint J6 position |
| $\overrightarrow{P_{J2}P_{J4,R}}$ | Vector from joint J2 position to real joint J4 position |
| $\overrightarrow{O_{PSI}P_{J4,R}}$ | Vector from arm angle orientation to real joint J4 position |
| $\overrightarrow{O_{PSI}P_{J4,V}}$ | Vector from arm angle orientation to virtual joint J4 position |
| $A_{PSI}$ | Arm angle: The angle between $\overrightarrow{O_{PSI}P_{J4,R}}$ and $\overrightarrow{O_{PSI}P_{J4,V}}$ |
| $D_{arm}$ | Distance from the origin to the circle of possible joint J4 positions in World 1 |
| $D_{buff}$ | Distance through which the collision buffer extends (user determined) |

Figure 10:
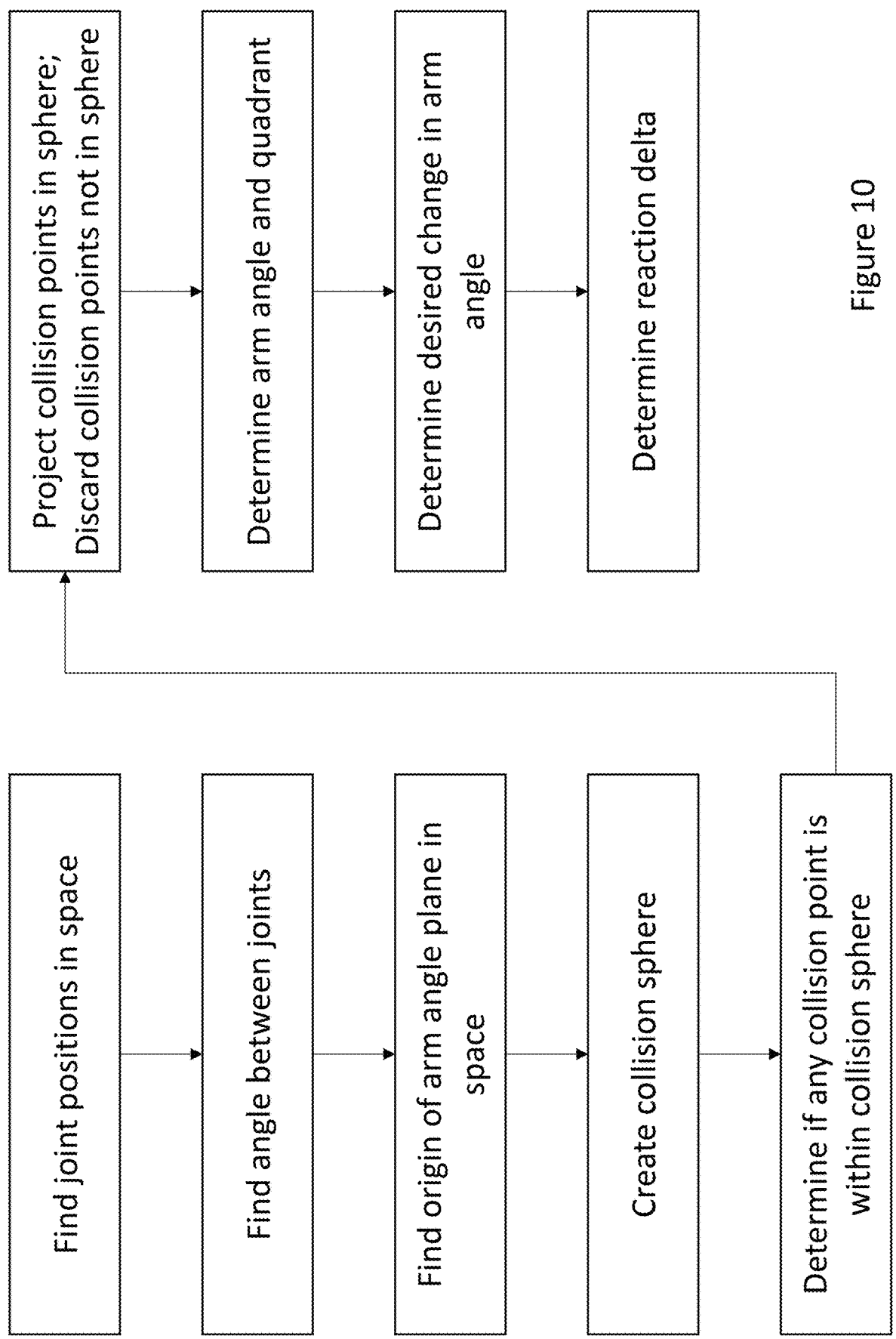
FIG. 10 illustrates a method for determining an arm angle of a robot.

FIG. 10 illustrates an example method for determining an arm angle based on the above hazard avoidance discussion. According to this method, collision avoidance can be completely agnostic to a task an instrument held by the robot is engaged in, and can operate independently of whatever task is being commanded by the robot programmer or operator. Moreover, the method does not require a robot to slow down or stop when a person (or other object) approaches. Rather, as long as the robot is aware of a person's dynamic position, the robotic arm may be continuously adjusted to avoid collision.

As seen in FIG. 10, an origin of the arm angle plane is first determined by finding the joint positions of the robotic arm in space, and then finding an angle between the vectors $$\overrightarrow{P_{J2}P_{J6}} \text{ and } \overrightarrow{P_{J2}P_{J4,R}}.$$

This angle can be determined according to:

$$\theta_{J24,J26} = \cos^{-1}\frac{\overrightarrow{P_{J2}P_{J6}} * \overrightarrow{P_{J2}P_{J4,R}}}{\left\|\overrightarrow{P_{J2}P_{J6}}\right\| * \left\|\overrightarrow{P_{J2}P_{J4,R}}\right\|}$$

The origin position of the arm angle plane in space can then be determined according to:

$$O_{PSI} = x_0, y_0, z_0 = P_{J2} + \left(\frac{\left\|\overrightarrow{P_{J2}O_{PSI}}\right\|}{\left\|\overrightarrow{P_{J2}P_{J6}}\right\|} * \overrightarrow{P_{J2}P_{J6}}\right) \text{ where } \left\|\overrightarrow{P_{J2}O_{PSI}}\right\| = \frac{1}{2}$$

because the distance between joints J2 and J4 is equal to the distance between joints J4 and J6, and $$\overrightarrow{O_{PSI}P_{J2}} = \frac{-1}{\left\|\overrightarrow{P_{J2}P_{J6}}\right\|} * \overrightarrow{P_{J2}P_{J6}}.$$

Next, a collision sphere is created having a radius equal to $D_{arm}+D_{buff}$, where $D_{arm}$ is determined by solving the right triangle generated between joint J4, joint J2, and the arm angle origin. That is, $D_{arm}$ can be determined according to:

$$D_{arm} = \sin\theta_{J24,J26} * \left\|\overrightarrow{P_{J2}P_{J4,R}}\right\|$$

Whether a collision point is within the collision sphere can be determined by comparing the distance from the origin to each point to avoid in World 1 to the radius of the collision sphere. Points not within the collision sphere can be discarded, while points within the collision sphere can be projected on the plane defined by the intersection of $$\overrightarrow{P_{J2}P_{J6}}$$

with the arm angle origin (the movement of the robot elbow being restricted to this plane) to create an image of each point on the plane.

The projection of the collision points within the collision sphere can be accomplished according to the following algorithm:

a. $\overrightarrow{O_{PSI}P_{J2}} = \langle A, B, C \rangle$ b. Plane EQ: $Ax+By+Cz=Ax_0+By_0+Cz_0$ c. Image on plane will be the point $I_n=(\alpha, \beta, \gamma)$ d. Given a point in space denoted by $(x, y, z)$, a vector can be defined that is orthogonal to the arm angle plane and leads to the given point in space, denoted as: $\langle x-\alpha, y-\beta, z-\gamma \rangle$ e. The vector of d. will be parallel and proportional to

such that $$t * \overrightarrow{O_{PSI}P_{J2}} = \langle x-\alpha, y-\beta, z-\gamma \rangle$$

f. Therefore:
  i. t*A, t*B, t*C=x−α, y−β, z−γ
  ii. t*A=x−α→α=x−(t*A)
  iii. t*B=y−β→β=y−(t*B)
  iv. t*C=z−γ→γ=z−(t*C)
g. Given the above information known about the plane vector, origin location, and the given point in space, the value of t can be solved for by plugging the image into the plane equation:
  i. A(x−(t*A))+B(y−(t*B))+C(z−(t*C))=Ax$_0$+By$_0$+Cz$_0$
  ii. −1(A$^2$+B$^2$+C$^2$)t=A(x$_0$−x)+B(y$_0$−y)+C(z$_0$−z)

$$t = \frac{A(x_0-x)+B(y_0-y)+C(z_0-z)}{A^2+B^2+C^2} \quad \text{iii.}$$

h. Once t is determined, it is possible to back solve for I$_n$=(α, β, γ) by plugging t into the equation derived in 3.e.ii-iv.
i. Repeat for each point within the collision sphere.

Once the collision points are determined and projected, an arm angle can be calculated. The arm angle is defined as the angle between

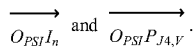

Both of these vectors lie on the arm angle plane, where the origin of the arm angle is

However, because the calculation of the angle between these two vectors returns the absolute value of the angle, the appropriate quadrant of the angle is determined in subsequent steps. To determine the quadrant of the arm angle plane that the image is in, a second plane is created containing

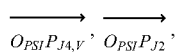

and O$_{PSA}$. The image of each point I$_n$ is again found on this new plane. In doing so, only the value of t needs to be determined, and the sign of the ratio value of t is determined as sign of the arm angle.

The arm angle values and the magnitude of vector ⟨x−α, y−β, z−γ⟩ are then used to determine a desired change in arm angle (reaction delta) that is used to calculate the arm angle reaction due to the collision point. The reaction delta follows the general linear formula Δ=−m*|x|+b, with negative values filtered out. The value m is a constant that determines how far away from the collision point the robot will react, the value x is the distance between the current arm angle and the arm angle mapping of the collision point, and the value b is an offset that controls the magnitude of the reaction. B may be defined as $$b = \frac{D_{max}+P_{min}}{Z_{augmented}},$$

where $D_{max}$ is a maximum desired reaction, $P_{min}$ is a diameter of the robot joint if modeled as a sphere (accounting for the fact that the collision point cannot be inside the robot), and $Z_{augmented}$ is an augmented distance from joint J4 to the collision point. The augmented distance reduces the effect of distance on avoidance as the point falls away from the reference plane. Due to the restriction of joint J4 to the reference plane, it is less important to avoid points that are far away from this plane. The distance is calculated in the coordinate system of the reference plane and is determined as $Z_{augmented}=\sqrt{x^2+y^2+(Az^2-Bz)}$. Here A and B can be chosen based on robot-specific dimensions. In one example, A=0.005 and B=0.05.

Figure 11:
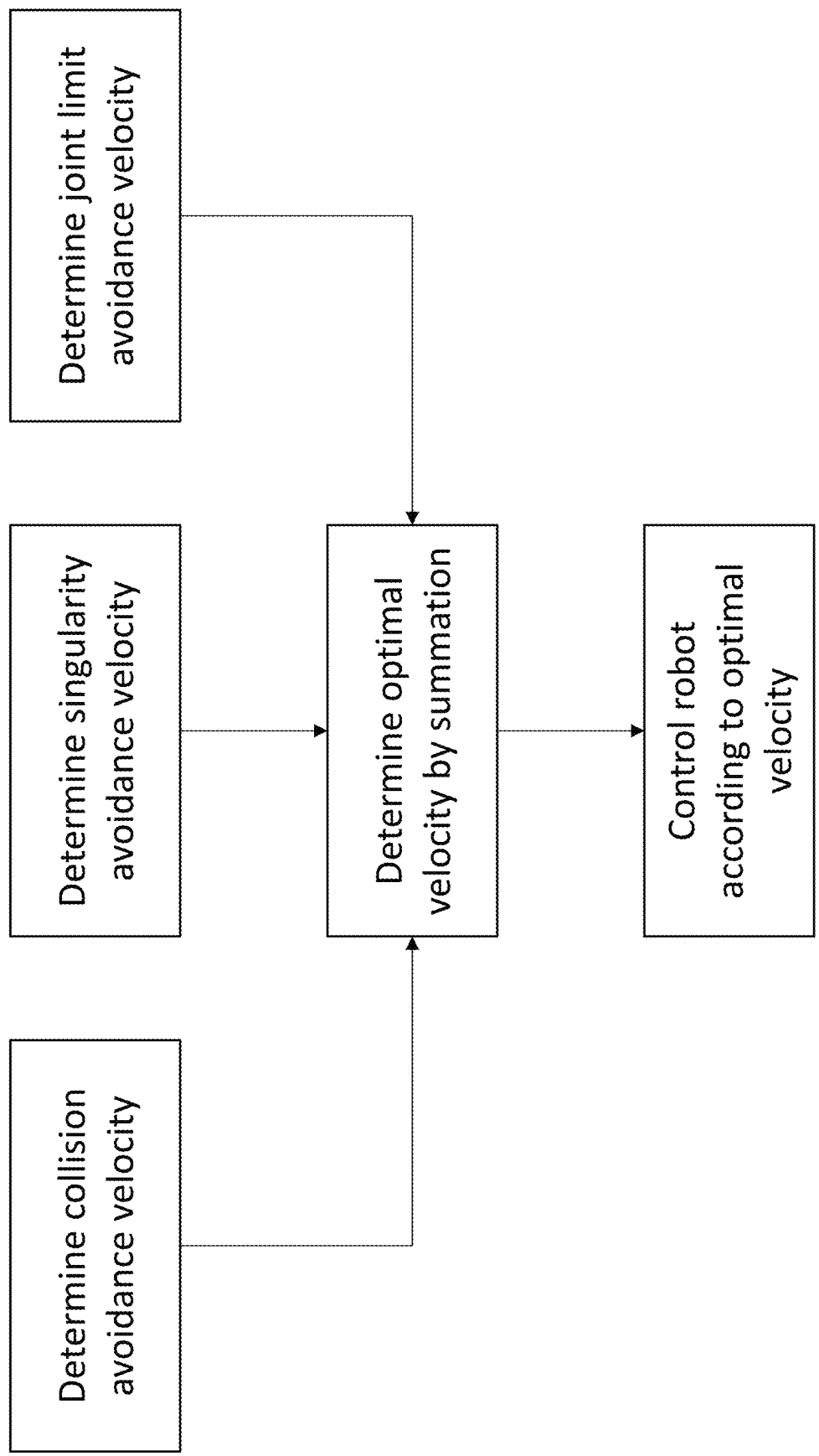
FIG. 11 is a flow diagram illustrating a method for determining velocity control of a robotic arm.

The delta that is calculated can be added to the current arm angle to produce a new arm angle that is converted into a joint J3 velocity. A maximum acceleration of a new delta may be capped to create a trapezoidal velocity profile to smooth acceleration. This further helps prevent Cartesian position drifting when the direction of arm angle avoidance rapidly changes. With reference to FIG. 11, an appropriate velocity function is determined for each of the arm angle positions determined by the avoidance functions. The three velocities are then summed to calculate a single optimal velocity for the redundant axis to drive avoidance of all hazards. The robot can then be controlled according to this optimal velocity.

The above-described 7-DOF control is not only applicable to a single robot in a clinical setting; rather, it can be applied to any number of robots working in a collaborative space. This method can optimize the pose of each of the robots for internal considerations (joint limits and singularities) and external considerations (preventing itself from running into neighboring structures, robots, or people). Further, the above method can be used in any setting, including clinical surgical robotic settings and industrial manufacturing settings.

It is also noted that in some embodiments, the 7-DOF control may be produced by a trained machine learning system. For example, such a system may be trained to output relevant collision (or other avoidance) points (including anatomical regions to avoid), new arm angles, joint positions, velocities, and accelerations based on input current arm positions and references, object positions and references, and the like.

Another aspect of the present disclosure relates to the coordination of movements of multiple robots. Referring back to FIG. 1, the coordination may be performed through a coordinator-dependent framework, where the coordinator controller 102 is responsible for exchanging information with any number of dependent controllers 104, each locally controlling a robot 106. The dependents 104 rely on the coordinator 102 to command actions, send and request information, and provide continuous data for executing tasks. The coordinator 102 relies on the dependents 104 to respond to commands, send requested information, and provide continuous data required for the coordinator to manage activity execution and synchronization appropriately.

With this framework, the surgeon 110 can manage a surgical procedure of coordinated tasks through the HMI 112, which displays a procedure flowchart and like information, patient models, images/videos of the surgical procedure, patient vital signs, and the like, and receives inputs adjusting the flow and execution thereof. In other words, the HMI 112 can serve as a translator, communicating to the coordinator 102 the activity that is to be executed. The coordinator 102 then coordinates the execution of that action, communicating commands to the dependents 104 and in turn to the robots 106.

By way of more specific example, the coordinator-dependent framework can assist with safety monitoring by individual dependents 104 communicating their health information to the coordinator 102, so that the coordinator 102 can manage the totality of information and command appropriate responses from the dependents 104. Additionally, the coordinator 102 can communicate the health status of the dependents 104 to the group so that each dependent 104 can execute its own safety monitoring that is dependent on the group's health. Local safety monitoring may be handled by the individual dependents 104. This safety is driven by the limits set in individual activities. These limits can be assigned by the coordinator 102 but handled by the individual dependents 104. Additionally, the coordinator-dependent framework can assist with collision avoidance between the robots 106 themselves, and between robots and other objects in a setting (e.g., an operating room). Individual dependents 104 can stream their own collision point data to the coordinator 102, which can then aggregate the collision data and communicate the collective collision data to the group so that each dependent 104 can execute its own collision avoidance that is dependent on the pose of all robots 106. Additionally, the coordinator 102 can manage static collision points and publishes them to network shared variables, accessible to all dependents 104.

The transfer of information and signals between elements of the system 100 enables synchronization of multiple robots 106 performing the above-described coordinated tasks, cohesive safety monitoring system, collision avoidance, and the transfer of data. Further, through the transfer of information between the elements of the system the coordinator 102 can manage selective time synchronization for any number of dependent robots 106 all performing coordinated tasks. In addition, the above framework supports a methodology for robot movement that can be paused or aborted based on real time data from any robot 106 in that group.

Figure 12:
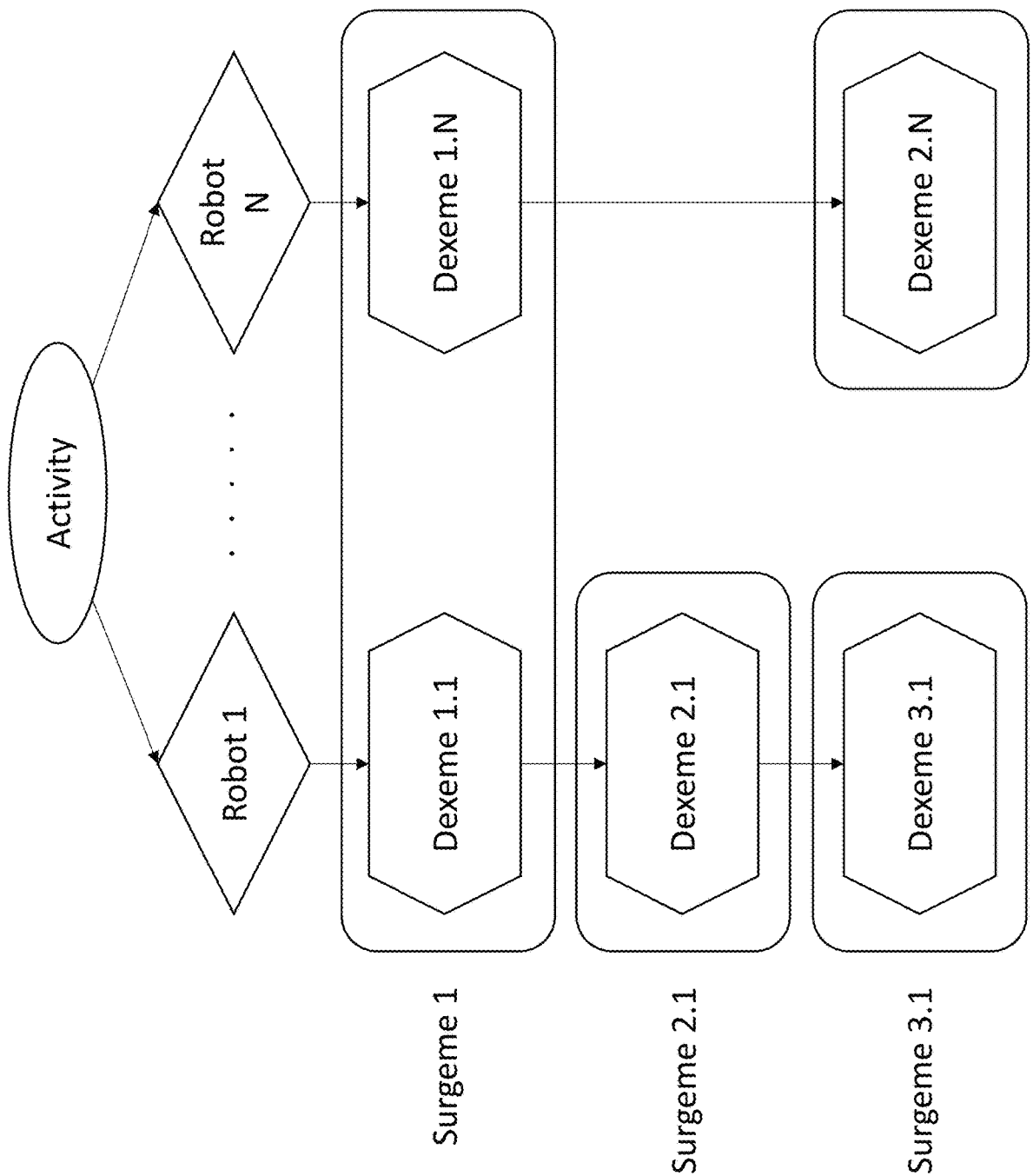
FIG. 12 illustrates the relationship between activities, surgemes, and dexemes.

In describing synchronization between robots 106, and with reference to FIG. 12, it is understood that a surgical procedure is a collection of activities and decision points therebetween. Each 'activity' is a surgical task (e.g., suturing) that is executed by one or more robots 106 synchronized through subtasks (e.g., grabbing the needle) referred to as surgemes. Transition surgemes may be generated in real time to connect one surgeme to another. Each surgeme is a collection of 'dexemes', which are sets of paths, trajectories, or other parameters given that cause an intended motion to be completed by an actuator. Each dexeme involves only one robot 106.

When performing automated tasks, a dexeme can be considered as a trajectory encompassing a series of setpoints in time (or alternatively a series of setpoints to be scheduled based on prescribed rates) where the desired motions and loads of the robot instrument can be explicitly defined. Any specific surgeme can include any number of dexemes, and the grouping of a collection of dexemes into a single surgeme is defined through synchronization groups.

Synchronization groups include specified dexemes that make up a surgeme that all follow specified synchronization parameters. In some embodiments, multiple synchronization groups can be created such that not all robots 106 are required to be synchronized for all activities. The synchronization parameters include a synchronized start, a synchronized end, and a synchronized clock. If dexemes start at the same time, then they have a synchronous start. Once a robot 106 is ready to begin their dexeme, they signal that they are ready to the coordinator 102. Once all robots within the surgeme have signaled that they are ready, a start command from the coordinator 102 may be sent at the same time to each robot 106 through their corresponding dependents 104 to ensure the synchronous start. In addition to waiting for included robots 106 to be available, a synchronization group might also rely on the completion of another synchronization group in order to start. For example, if robots 3 and 4 are executing a task that must be completed first or they are in an area that must be cleared before starting a surgeme involving robots 1 and 2, then robots 1 and 2 wait until the surgeme that robots 3 and 4 are executing is completed.

Similarly, in some cases dexemes within a surgeme should be terminated whenever any dexeme in that surgeme ends, even if prematurely. Such premature completion can be due to safety, but also could be because a termination criteria has been met. For example, a dexeme can end when a desired load on an actuator is met; and if a synchronized end parameter is set for the surgeme, the completion of that dexeme will result in the completion of all dexemes within that surgeme. A natural end may also be synchronize. For example, a retracting dexeme can be set to terminate when a cutting, excising, or reconstructing dexeme is completed, and thus retraction is no longer needed.

In order to ensure such synchronization of dexemes, a master clock (e.g., belonging to the coordinator 102) can be used in lieu of local clocks belonging to each robot 106 or corresponding dependent 104. In these cases, time is multicast to all robots 106 in the surgeme from the coordinator 102 or other location of the master clock. By using a common clock, it is possible to pause multiple dexemes if one dexeme is paused, and/or to adaptively modify times across multiple dexemes.

Figure 13:
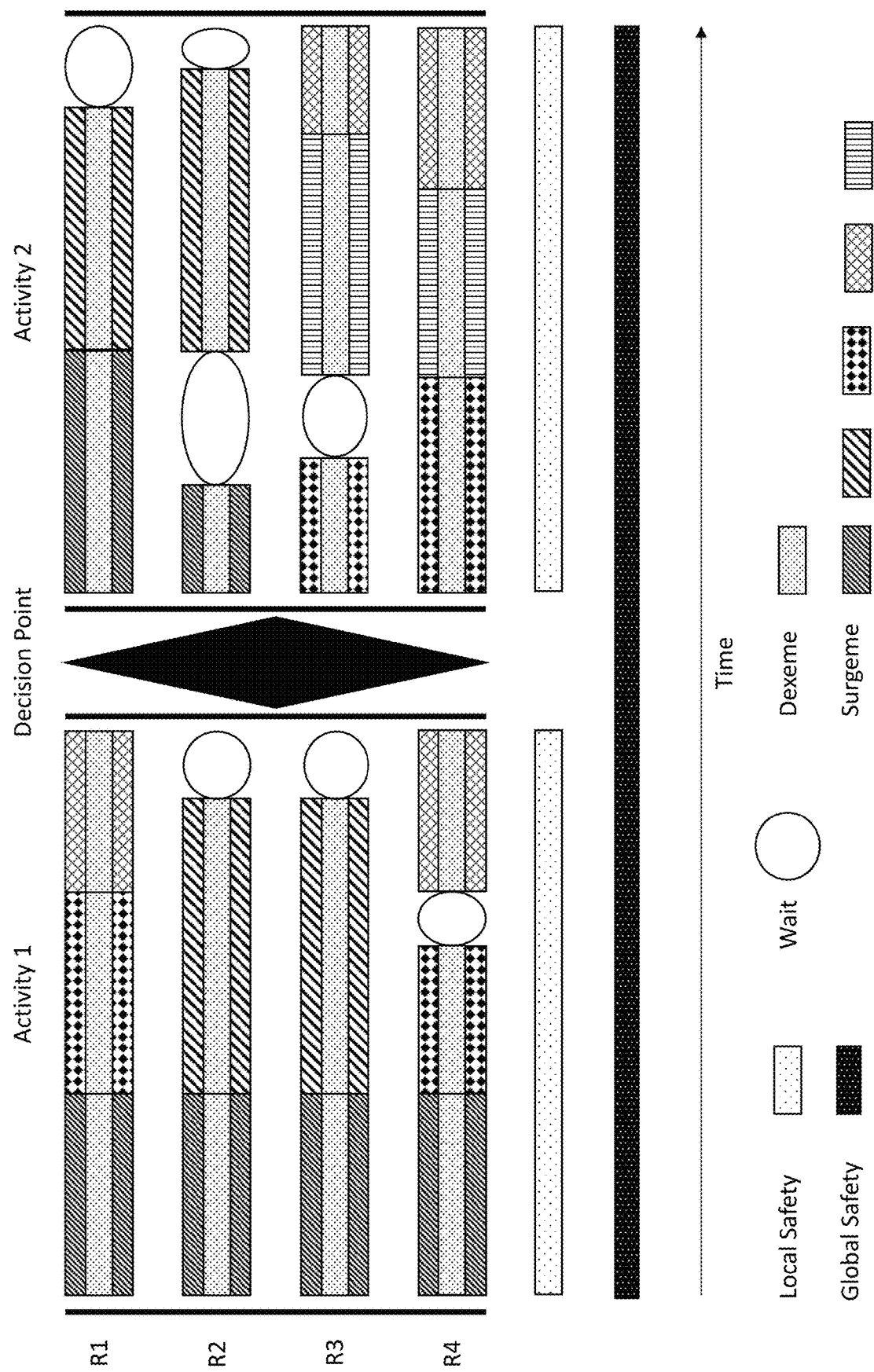
FIG. 13 illustrates dexemes, surgemes and activities in an example procedure.

FIG. 13 illustrates how dexemes, surgemes and activities fit into an example planned procedure. Therein, a series of dexemes and surgemes are shown for two activities, executed by four robots R1-R4. In Activity 1, each of the robots R1-R4 are grouped to perform a first surgeme having a synchronous end. Robots R2 and R3 then perform a surgeme having a synchronous beginning and end, while the second surgeme of robots R1 and R4 has a synchronous start but an asynchronous end. When the second dexeme of robot R4 is finished, robot R4 waits for the second dexeme of robot R1 to finish prior to a synchronous start for the third surgeme of robots R1 and R4. Activity 1 ends upon the completion of the third surgeme of robots R1 and R4.

Following Activity 1, the procedure waits for any transition conditions to be met at the Decision Point prior to beginning Activity 2. Robots R1 and R2 then jointly execute two surgemes, each having a synchronous start but asynchronous end. Similarly, the first two surgemes jointly executed by robots R3 and R4 have a synchronous start but asynchronous end. However, the third surgeme jointly executed by robots R3 and R4 have an asynchronous start, but a synchronous end.

During the procedure, a local safety monitoring process occurs individually for each activity. Meanwhile, a global safety monitoring process occurs over the entirety of the procedure.

The coordinator-dependent framework can rely on one or more of the following streams of information between the elements of the system 100. In a coordinator-dependent command stream, bidirectional information is only exchanged when the coordinator 102 sends or requests it. The coordinator 102 can request information (e.g., data files, trajectory sets, dexemes, adaptive compensators, and the like), send information (e.g., trajectory sets and dexemes, adaptive compensators, and the like), and send commands (e.g., prepare, run, pause, abort, skip, and the like). In a dependent health and status stream, unidirectional information is continuously streamed from each dependent 104 to the coordinator 102 at a set frequency. Information in the dependent health and status stream may include a health status of the dependent 104 and corresponding robot 106, dynamic collision points, and a trajectory execution status (e.g., running, waiting, preparing, aborting, skipping to next, paused, and the like). The data of the dependent health and status stream may be used by the coordinator 102 to help manage task synchronization and monitor safety. In a coordinator global data stream, unidirectional information is continuously multicast from the coordinator 102 to all dependents 104 at a set frequency. The data of the coordinator global data stream can include global sensor data (e.g., multiple dependents rely on the same sensor data), global health data (e.g., function of local health of each dependent and informs all dependents on the overall health of the system for safety monitoring), aggregated dynamic collision points (e.g., compilation of dynamic collision points for all dependent), and time (e.g., from global clock to ensure synchronization). Depending on the frequency, coordinator global data information can be output in a single stream or multiple streams. A dependent robot stream transmits control signals from the dependent 104 to the robot 106 for execution specific movements, and receives sensor information from the robot (e.g., position information, instrument information such as an applied force and/or position). Further, static data that should be accessible by the coordinator 102 and dependents 104 can be saved as a network shared variable, hosted on the coordinator 102. Such information can include static collision points and static registration parameters, and may be readable and writeable by the coordinator 102 and dependents 104.

A coordinator interface data stream communications data from the coordinator 102 to the HMI 112, for monitoring by medical personnel 110. Information of the coordinator interface data stream can include dependent status and health, model data, and other specific information that the HMI utilizes to run the user interface. Similarly, an HMI user sensor data stream communicates data from the HMI 112 to the coordinator 102, including any data for continuously updating the rest of the system, such as data from hardware and sensors connected to the HMI. Finally, an HMI coordinator command stream is a transactional communication between the HMI 112 and coordinator 102. These commands relate to the execution of a procedure, for example, including a next activity to execute, or specific controls for the robots 106.

The coordinator 102 can request data from the dependents 104 allowing for a complete compilation of data. All of the available data may be accessed by medical personnel 110 via the HMI 112. With this information, and the ability to send commands to the coordinator to in turn control each of the robots 106, the medical personnel 110 can interact with, control, and monitor the surgical system 100. Another job of the coordinator 102 is to manage the above-described synchronization between robots 106. The HMI 112 can send an activity to be executed to the coordinator 102. The coordinator 102 may then unpack the activity, and analyze the surgemes and dexemes therein. Based on the surgemes and dexemes associated with the activity, the coordinator generates trajectory (or like motion control) information (a trajectory plan) for each dependent 104 and associated robot 106. These trajectories and other movement data may be based on the above-described methods for optimization, collision avoidance, interaction with deformable objects, and the like. Commands for executed the movements are then sent from the coordinator 102 to the dependents 104 so that each dependent 104 and corresponding robot 106 can perform the associated dexemes for that activity in the appropriate synchronization/order. The coordinator 102 can also send any pause, stop, or abort commands to each dependent 104.

Another feature of the coordinator 102 is to manage the global safety monitoring system. The safety monitoring system detects any unscheduled events or actions by the dependents 104 or robots 106, and stops the system 100 from causing harm if such events or activities are detected. In one example, potentially harmful events or actions can be detected by monitoring sensor inputs and comparing them to expected values based on the current activity being executed. The global system may also prescribe and communicate robot-specific safety parameters to each dependent 104 for individual local safety monitoring.

The dependents 104 take the information communicated by the coordinator 102 and transform them into control signals that drive their corresponding robot 106. During each activity, the dependent 104 acquires a trajectory set of dexemes from the coordinator 104 and then waits for the coordinator's commands regarding what to do with the dexemes in the trajectory set sequence. Additionally, the dependent 104 receives collision avoidance data from the coordinator 102. This data can include all coordinates of objects (e.g., of other robots, of objects in the surgical room, anatomical areas, and the like) to be avoided by any portion of the system 100. This avoidance information can be used to drive the redundant joint of the robot to avoid a collision, as described above. This process of taking the trajectory sets and turning them into commands and robot movements is described in U.S. patent application Ser. No. 17/157,237 and Ser. No. 17/157,693, which are incorporated herein by reference in their entireties. The dependents 104 also perform local safety monitoring based on the robot-specific parameters received from the coordinator 102.

The above-noted HMI 112 can have multiple uses within the system 100. In one example, the HMI may provide an interface for medical personnel 110 to interact with and control the system 100. For example, such control may be based on a user-generated flowchart of a surgical procedure. The medical personnel 110 can interact with the HMI in any manner including, for example, through a touch screen or other monitor, keyboard, mouse, joystick, foot pedal, camera, throttle, eye-tracking, microphones, speakers, VR headsets, monitors, and the like. These inputs are then communicated to the coordinator 104 in the manners discussed above.

The procedure flowchart describes how a surgical procedure is to be executed by the robots 106 of the system 100, and can originate from preplanning as described in more detail below. As suggested in FIG. 13, the flowchart comprises two types of elements: activities and decision points. Activities are surgical actions that are executed by one or more surgical robots 106. Decision points act as branching points where tests or user input help choose the proper action to move forward. In other words, a decision point determines to which of two or more subsequent activities a surgical procedure should advance to. When the next activity is identified at the decision point, the decision is sent to the coordinator 102, which coordinates execution of that activity. Global sensor data, system health, and dependent dexeme status data communicated from the coordinator 102 to the HMI 112 help medical personnel 110 determine status and navigate through the flowchart. In some embodiments, the flow chart may be maintained at the coordinator 102, which automatically makes decisions at each decision point based on the available data to automate execution of the surgical procedure.

Prior to each procedure, a user can choose settings and configure the system 100 for a specific patient's procedure through the HMI 112. In one example, the user can import any or all necessary data for executing a customized procedure including, for example, simulation data regarding the patient's anatomy, setup, and equipment used to create the procedure. During this setup, the HMI 112 may also inform users equipment placement, sensor initializations, patient orientation, registration of robots and instruments, and the like. In some embodiments, setting up the operating room can be illustrated on the HMI 112 in a mixed reality interface where a simulated scene from the imported data displays a phantom overlay with reality. In some embodiments, the arrangement of elements may be displayed on a floor plan or like 3D model of the operating room. After setup, the HMI 112 may guide verification of connectivity in the equipment, any patient information, and any safety criteria.

The HMI 112 may also display a comprehensive virtual patient model that mimics the current state of the patient's tissues. These models may be registered to actual sensors on the patient during the surgery, as discussed above, such that the models are adjustable in real time to mimic the state of the biological tissue during the procedure. The models may be updated, for example, based on space warping method to mimic the defamation in the tissues. Another model can monitor a joint coordinate system and compare it to a world instrument position to focus on the adjusting model's local area compared to the instrument position. This approach can prioritize modifying the model area closer to the nearest tool to preserve computational power. Another method can use multiple cameras in real time to compare the biological tissues with the model. This method can find any discrepancies between the model and tissues to update the model or notify the user of differences. The virtual patient models may also be displayed on a screen, or as a mixture of virtual reality and physical reality. The mixed reality can allow for rendered virtual models to be overlaid onto a camera feed to highlight anatomical features. For example, predefined avoidance regions within the anatomy may be displayed via the HMI 112 (e.g., overlaid on real time intraoperative images or an anatomical model) to the medical personnel as a visual reminder of anatomical features to avoid.

In some embodiments, the avoidance region may be shown in a first visual manner (such as with hatch marks, stippling, in a red color, or the like) that is different than a second visual manner showing an acceptable operable region (e.g., in green or uncolored). Still further a third visual manner may be used to denote additional information. For example, a trajectory or like surgical path, cut margin, or the like may be illustrated as the second visual manner (since it may be considered acceptable), or in a third visual manner such as a line (dashed, black, or the like). Using a third visual manner can help make the additional information more visible within the acceptable region.

An activity's ideal surgical path could also appear in a mixed reality scene when the system is in teleoperated, as a guide for the medical personnel 110. The path may also include directional information, illustrated by arrows along the path. If the system 100 is in a collaborative or autonomous mode, then the planned course appears, so the medical personnel knows where each robot intends to move. Similarly, cut or excision margins may be shown when tissue or tumors are excised or cut.

In some embodiments, the HMI 112 may also record a procedure, including the data and commands of the various controllers of the system 100, video of medical personnel, trajectory information of the robots 106, displays of the HMI 112, procedure flows, and the like. Such information can be maintained for records, for playback to review the surgery, and/or training of medical personnel 110 and/or the above-described machine learning systems. Further, these recordings may be timestamped and include voice or other notes associated with the time stamps.

Similarly, the HMI 112 can display analysis reports of a surgical flowchart's execution and give the user statistics regarding the outcome. Such statistics may relate to a length of surgery, amount of time cutting, the total length of cuts, and the like. Cost (financial cost of materials, total time, and the like) can also be analyzed to provide an efficiency score of the procedure. Accuracy and error can be determined based on comparison to pre-operative simulations to identify how accurate the execution of the procedure was. Such outputs can further be used to train new surgeons or improve experienced surgeons' skills.

Joysticks of the HMI 112 may be configured for auto-clutching, such that the clutch repositions the joystick without moving the robots 106 to adjust for physical limitations in human joints and workspace limits. Accordingly, the system 100 may recognize when joint space and human limits are reached and adapt to the operational field. When the user exceeds limits and holds the joystick position, the controlled robot 106 can continue to move in a low-speed velocity mode. This control feature can effectively adjust the field of operation of the joystick. In this manner, the robot 106 does not have to stop moving to be changed and speed up a procedure.

The HMI 112 may also provide a "snapping" effect where a user's controls "snap" to a determined position as it is approached. Such a control allows a user to increase precision in their controls by, for example, predefining a snapping point. Such controls can be applied to robot movements, camera positions, or any other objects controlled by the HMI 112. Once the "snapped" position is reached, further micro adjustments may be made by the user. More particularly, a user may control rates of execution of movement. Providing a slower rate allows more precise control such that the micro adjustments may be made.

In some embodiments, a user may guide autonomous movements of objects, such as the robots 106. For example, a user may select individual buttons that correspond to activities, surgemes, dexemes, or the like, in a surgical flowchart. In other words, a user effectuate the start of an action or series of actions by a robot 106 that are automatically controlled by the system 100 once started. For example, if additional bleeding occurs, the user may press a button that applies additional suction to the workspace. In another example, a user may press a button indicating the decision made at a decision point.

Cameras of the HMI 112 may be stereoscopic camera feeds that generate 3D video to render a 3D virtual scene. 3D rendered objects and models can be displayable over top of the stereoscopic camera feed. 3D scenes may be displayed on 2D monitors, VR headsets, and the like. Various control devices, such as the joysticks, may have six degrees of freedom to generate the proper commands to control the robots 106. The control devices may also have haptic feedback to alert the user of movements of the robot 106, of interaction between the robot instrument and the patient's tissues, and the like. Given the patient's known anatomy, it is possible to give accurate haptic feedback data based on the tissue's mechanical properties.

Figure 14:
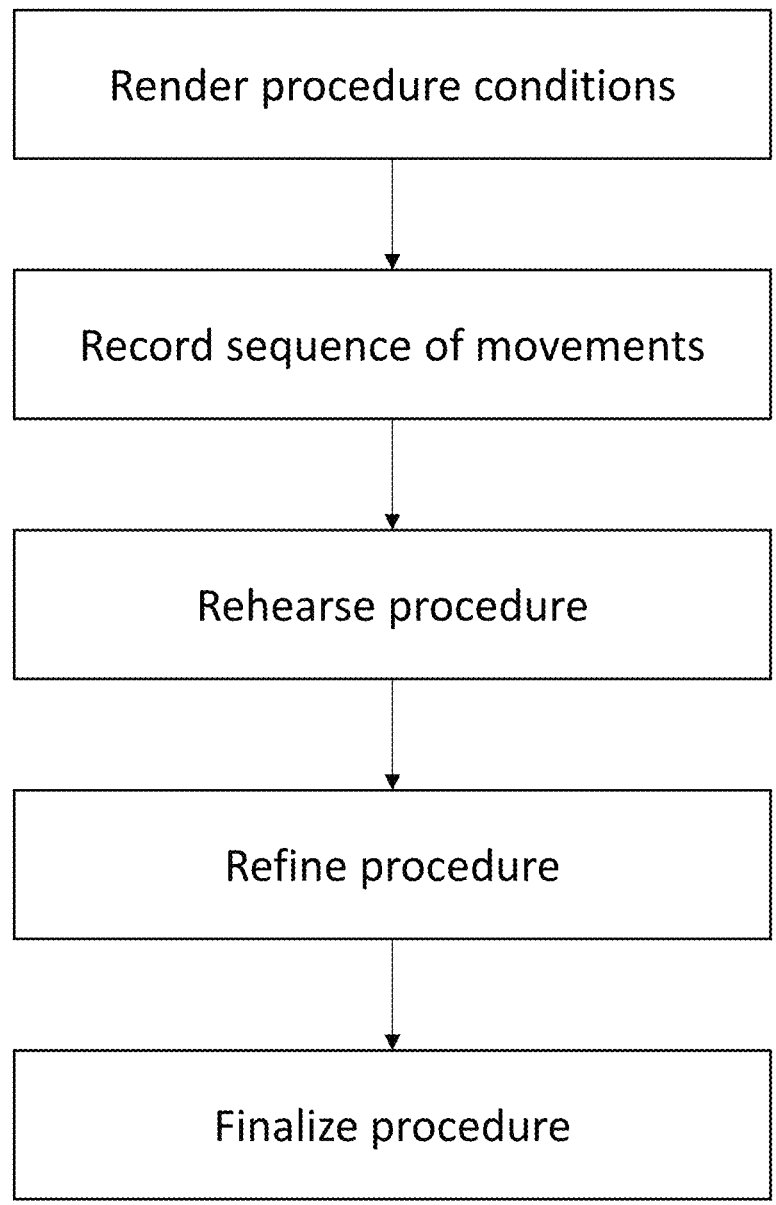
FIG. 14 illustrates a process of a pre-operative platform for autonomous or robot-assisted surgical procedures.

Another aspect of the present disclosure relates to a pre-operative platform for planning, refining, and generating a sequence(s) of robot movements for autonomous or robot-assisted surgical. Such a platform follows, for example, the procedure illustrated in FIG. 14. As shown therein, the process includes first rendering conditions of the procedure, then recording a sequence of a predefined movements and configuring the surgical robotic system, rehearsing the procedure virtually, refining the procedure to increase efficiency and eliminate unnecessary movements, and finally reporting a finalized procedure for in vivo execution.

In one example, rendering can involve generating an in silico scene to mimic the conditions present during a specific patient's procedure. Rendering may be of the operating environment and/or the patient.

The scene rendering of an operating environment may be performed by one or computers in which a user (such as the medical personnel or surgeon) can drag, drop, and move objects in a virtual space commonly seen in a surgical operating environment to mimic the operating room that the individual patient will use. The objects may be dynamic (e.g., those that can move, change shape, and displace via dynamic meshes and joints, such as robots, cameras, end effectors, instruments, and the like) or static (e.g., rigid bodies that do not move such as tables, cabinetry, carts, workstations, and the like). Render the environment allows for accurate spatial representations and relationships of the objects and their positions in the workspace for movement planning considerations (e.g., robotic collision avoidance). The rendered scene can be viewable for example via a 2D screen or through a virtual reality device.

Once rendered, the scene may be optimized to suggest an ideal workspace arrangement. Such a workspace allows for the greatest field of motion inside the patient, minimizes the chance of collision between objects during the procedure, and provides the greatest freedom for the robotic linkages used in the procedure to avoid joint limits or singularities.

Rendering of the patient may include an anatomically correct 3D representation of the patient and any tissues being operated on. These renderings may be based on sensor or imaging (e.g., CT and/or MRI) data from the patient. Further, different physical properties may be applied to the various types of tissues to mimic their real-world interaction with objects, such as the instruments utilized during the procedure. These physical properties thus can include mechanical properties or visual properties of the tissue. Anatomical features outside a region of interest (e.g., the region the procedure is performed on) may be generalized with a prefabricated model that is scaled to be proportional to the patient's height and weight in order to preserve computational power during the simulation.

Recording the procedure may involve generating a sequence of predefined movements and configuring the surgical robotic system accordingly. To facilitate the quick and efficient creation of procedures, the framework can be configured to import templates of common procedures, activities, surgemes, dexemes, and/or motion profiles of individual robots. These templates may have been previously optimized, deemed safe, and/or otherwise evaluated as acceptable. Additionally, a user can create new procedures, activities, surgemes, and dexemes by defining specific individual motions of the robot or by arranging the above-noted templates.

New motions may be defined by, for example, using motion tracking to track a surgeon's tools as they perform a task or to record a teleoperated robotic surgical instrument as a surgeon performs a task; recording a surgical instrument's or robot's reported cartesian positioning to create a motion profile while executing a teleoperated surgical task or recording a surgical instrument's or robot's joint positioning to make a motion profile while performing a teleoperated surgical task; recording forces exerted during a teleoperate robotic surgical task or during a surgical task executed by hand; and/or recording deformation of the anatomy during surgical task execution or utilizing sensor fusion to determine and record the state of the anatomy during the performance of a surgical task.

The above tracking and recording can be from surgical tasks performed on previous patients, cadaveric specimens, animal subjects, 3D printed anatomical models, and the like. Further the data collected from the above tracking and recording may be from force, vision, motion, electromagnetic, radioactive, biometric impedance, temperature, and like sensors. The system may then translate this data associated with each tracking and recording (e.g., gain profiles, kinetics, positions, and the like) into individual motion profiles. Each profile may be then collected into a dexeme, surgeme, activity, and/or procedure. This data may also be utilized to generate or evaluate decision points and/or for local/global safety monitoring criteria.

A procedure editor allows the user to create, edit, and otherwise organize the individual movements, dexemes, surgemes, activities and decision points into the procedures. Each of these elements may be displayed to the user in the form of one or more flow charts, in which each element can be arranged by a "drag and drop" style user interface. Each element can also be selected and expanded to give more specific information. For example, one flow chart may illustrate a procedure as a series of activities and decision points. A user may then select and expand an individual activity on the procedure flow chart to display that activity as a series of surgemes. Similarly, selecting and expanding each surgeme may further display the flow of the individual dexemes therein, and selecting and expanding each dexeme may display the individual series of motion profiles therein.

Figure 15A:
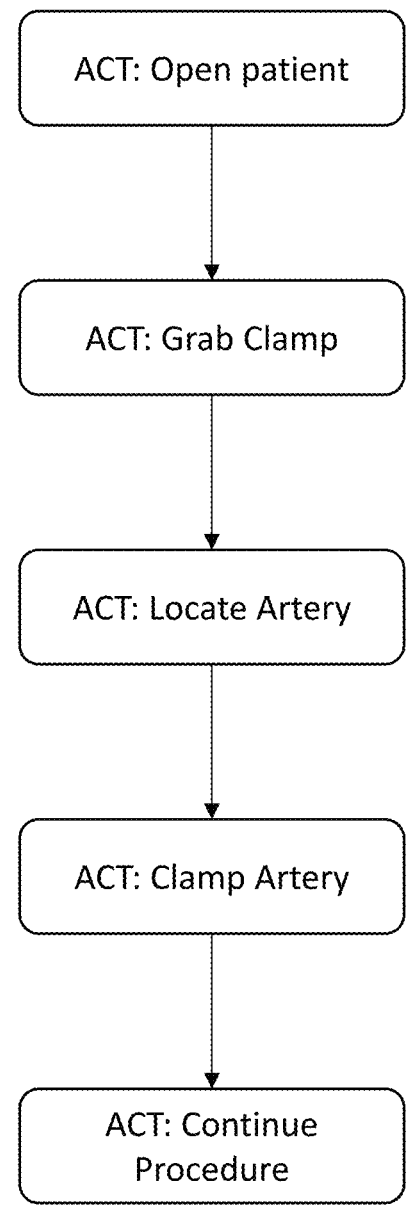
FIGS. 15A and 15B illustrate example surgical procedure flow charts.
Figure 15B:
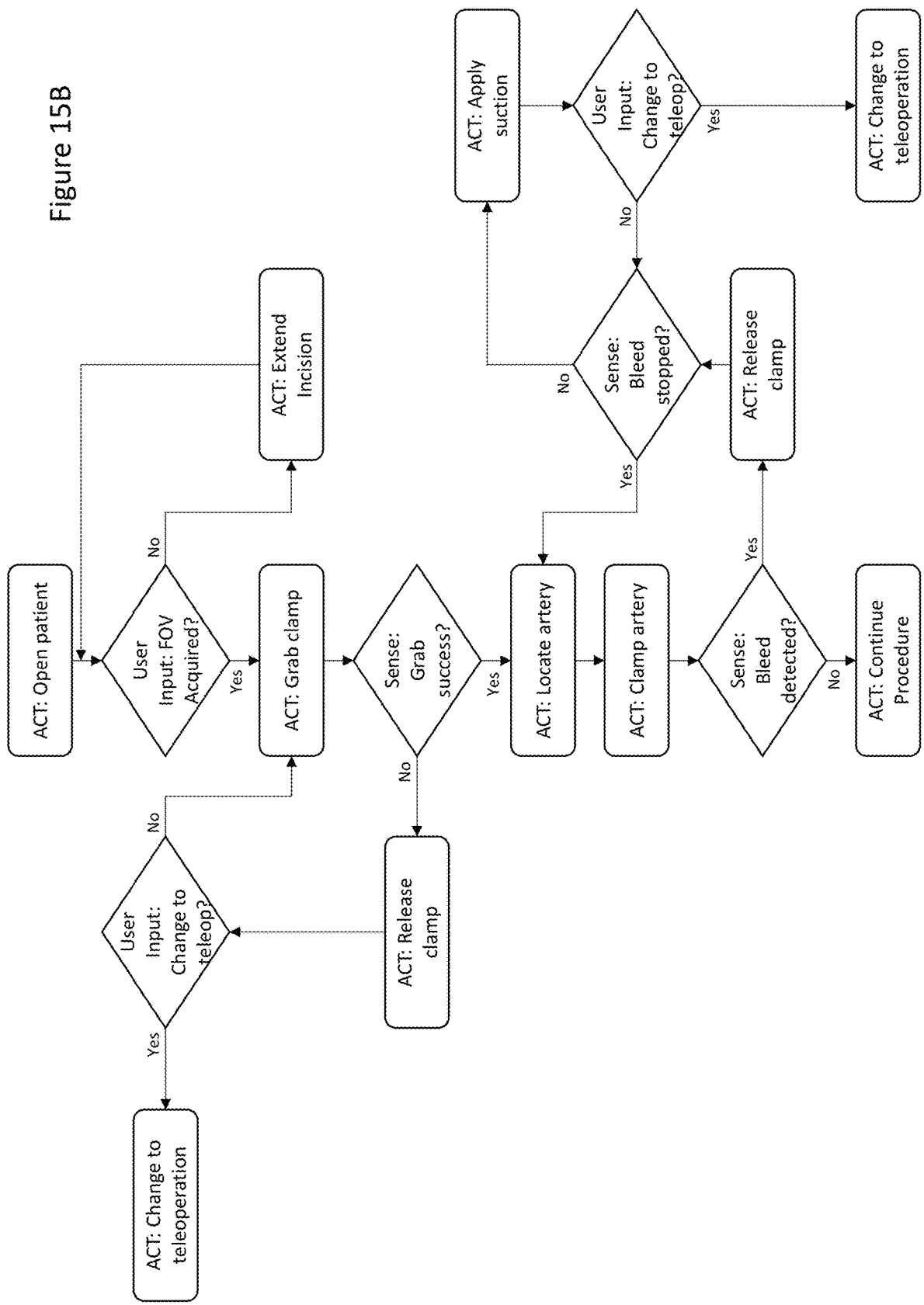

Example flowcharts of the procedure editor are illustrated in FIGS. 15A and 15B. Both FIGS. 15A and 15B illustrate a procedure that includes clamping an artery. FIG. 15A first illustrates a non-decision based version of the procedure, which the procedure advances through a series of activities linearly. As seen therein, the procedure begins with the activity of opening the patient, and then proceeds to the activity of grabbing a clamp. With the robot holding the clamp, the procedure locates the artery to be clamped and then performs the clamping activity. Once the artery is clamped, the procedure can proceed to any additional activities.

FIG. 15B illustrates the same procedural flow but with decision points between actions. Of note, the linear path of FIG. 15A generally remains in the middle of the flowchart in FIG. 15B. However, a first decision point between the act of opening the patient and grabbing the clamp is based on whether a proper field of view (FOV) has been acquired. In other words, is the incision large enough to provide proper access for the remainder of the procedure? Here, the decision is based on a user input. For example, a medical personnel 110 may be prompted on an HMI 112 to identify whether FOV is appropriate via a pop-up window with buttons representing "yes" and "no". Depending on the decision, further input may be requested. For example, in the event the FOV is not appropriate, the decision may also request the user to input via the HMI 112 (e.g., with a controller, or drawing on a visual representation of the incision site) a desired incision path to achieve an appropriate FOV. The incision may then be extended, and the decision represented. In other embodiments, the decision may be automated based on image analysis of the incision. Once the appropriate FOV has been determined, the procedure proceeds to grabbing the clamp. If sensors determine (e.g., based on locations of the clamp by position sensors or image analysis, appropriate forces are detected, or the like) that the glamp was not successfully grabbed, the clamp is released and the user is presented with another decision of whether to control the robot tele operatively. That is, the user is presented with the option of taking control of the robots manually to perform the clamp grab. If the user elects to manually control the robot(s), the procedure flow may be re-entered at any location.

If it is determined that the clamp is successfully grabbed, the artery is located and then clamped according to those activity definitions. If sensors or a user then determine bleeding in the patient (thus indicating a poor clamp), the clamp is released. If it is determined that the bleeding has stopped, the procedure can again locate the artery and attempt to re-clamp the artery. If the bleed has not been stopped, suction is applied to the bleed and the user is asked whether they wish to teleoperatively control the robots to stop the bleeding. Once the artery is clamped and no bleed is detected, the procedure can then continue.

As noted above, each action and decision point and the connections therebetween may be adjusted pre-operatively or in real time by a flowchart editor. This may be accomplished in one embodiment by simply "dragging and dropping" each element of the flowchart based on defined activities and decision points. Should a user wish to modify the activity definitions, each activity may have a flowchart similar to that of FIGS. 15A and 15B (with the corresponding surgemes and dexemes), or charts similar to those illustrated in FIGS. 12 and 13. Again, however visually presented to a user, the elements (activities, surgemes, dexemes, motion profiles) can be modified visually to adjust the actions performed by the robots. While editing, the system may be configured to analyze the procedure in real time to identify any potential errors or improper combinations of activities and decision points. For example, it would not be appropriate to clamp an artery without first identifying the artery or grabbing the clamp. In the event an impropriety is detected, the editor may suggest or automatically change the procedure. Users may also provide comments to the flowchart for later review and discussion.

Similar to identifying improper activities, the above-discussed safety monitoring system may be configured to sense and manage unscheduled events based on the procedure flowchart. Even though the procedure flowchart's decision-based architecture can handle contingencies, it is not guaranteed to cover every possible scenario in surgery. A safety monitoring system can thus analyze the procedure based on a given flowchart and monitor any unscheduled events, such as additional bleeding, increase/decreased blood pressure, increased/decreased heart rate, unexpected oxygen saturation changes, instrument malfunctions, excess forces, unexpected visual properties, or unexpected anatomy. This monitoring system can employ multiple levels of control. At the highest level of control, the system can have the ability to override an automated procedure. Lower levels of control may simply display or sound a warning when criteria are triggered, or give the medical personnel the ability to change into a fully teleoperated control mode. The levels of control may be separately defined for each event. These criteria can help determine whether to continue, come to a controlled stop, or come to an emergency stop. Additionally, the safety monitoring system can apply an adaptive compensation to dexemes to adjust the trajectory and motion profile of a robot in real time to adapt to any potential or detected events.

The global safety monitoring system may be set to run continuously during the simulation or execution of the procedure, spanning multiple activities. This level can monitor the highest levels of motion, such as tracking the occurrence of an unscheduled event. The criteria of the global system may not change through the course of the procedure. In contrast, the local safety monitoring system applies to execution each activity, surgeme, and/or dexeme individually. The criteria monitored by the local safety system can be directed to activity-specific or movement-specific issues that may occur, such as making sure a specific force profile is not exceeded during a cut, excision, or reconstruction.

These criteria (and resulting actions) for each safety system may be determined and set during the procedure planning based on past procedures and activities, or manually input by a user. For example, the user can identify a sensor state associated with a fault (e.g., a force threshold, positional limit, and the like). Further, termination criteria can be determined for each fault, or for multiple levels of fault. For example, a user may define that for a first threshold of force detected, the medical personnel are simply presented with a warning or option to take teleoperative control; for second higher threshold of force detected, a controlled stop is initiated; and for a third even high threshold force detected, an emergency stop is applied to the system. In other example, a similar progression of warning, controlled stop, and emergency stop may be applied if robot movement velocities or accelerations increase above defined thresholds, or if robot or instrument positions approach or enter avoidance regions (either in the operating environment by the robot, or an anatomical region by the instrument). To further ensure safety, medical personnel may always have the ability to enable manual control of an automated robot actuator.

Once the procedure has been created, it may be simulated in a virtual or physical setting. Virtual simulations may include a 3D virtual visualization of the procedure so that the user can view the procedure in time via video manipulation tools like play, pause, fast forward, rewind, and the like. Additionally, the user can interact with the flowchart to jump to different sections of the simulation. This system can simulate both the physical state of the robot and the physical and physiological state of a patient at any given time. The simulation described here can be produced to be viewable via a 2D screen or through a virtual reality device. The physical simulation may be performed on a physical specimen (e.g., cadaveric specimens, animal subjects, 3D printed anatomical models) on which an automated robotic surgical system can execute the procedure.

Based on the simulations, the procedure may be refined (e.g., optimized) to increase efficiency and eliminate unnecessary movements. This optimization may be performed at least in part as earlier-described based on machine learning as applied to any level of the procedure (e.g., activities, surgemes, dexemes, and movement profiles/trajectories). In some embodiments, the unnecessary movements may alternatively or additionally be identified by tracking the simulation. The optimization may be performed during the simulation or after. For example, if an unnecessary movement, activity, or the like is identified during the simulation, the user may pause the simulation to remove the unnecessary action, and then resume (or repeat) the procedure. Optimization can also take the form of determining how to pair subsequent dexemes, surgemes, or activities to create new actions that a robot, but not a human operator, can execute.

Finally, a report of the (optimized) procedure may be output for final review by a user. Similar to the reports described above with respect to a medical personnel's performance during a surgical procedure, this report may provide an analysis of the simulation outcome or predicted outcome (if no simulation is performed). Such statistics may relate to a length of surgery, amount of time cutting, the total length of cuts, and the like. Cost (financial cost of materials, total time, and the like) can also be analyzed to provide an efficiency score of the procedure. Accuracy and error can be determined based on comparison to pre-operative simulations to identify how accurate the execution of the procedure was. Such outputs can further be used to train new surgeons or improve experienced surgeons' skills by evaluation. Further, the system can compile the flowchart into a series of control signals for each associated robot to generate an executable procedure in the form of a series of trajectory plans for each robot. In other words, similar to how source code may be compiled to form a software program executable by a computer, the procedure flowcharts may be compiled into a list of commands executable by dependents 104 and robots 106 that result in the execution of the procedure via motion of the robot according to the determined trajectory plan.

The above planning framework and system architecture overcome current limitations of purely tele-operated systems, to become an autonomous or collaborative system. The features herein facilitate a system that can interpret and use real-time sensor data to execute a surgical procedure in which communication latency and security risks do not pose the same barriers to the surgical as in teleoperations over large distances using the Internet or other preexisting communication networks. In other words, a system that is capable of being taught (through surgical planning) on virtual surrogates for patient specific anatomy can operate remotely and autonomously on that patient and utilize learned specific surgical maneuvers for some or all of the surgery. With only the supervision of a human surgeon, the pre-learned complex surgical maneuvers used throughout the surgery would not be susceptible to communication latency that might otherwise cause the robot to move in an undesirable way.

Further, the above-described pre-operative planning information, reports, procedure flowcharts, and executable procedures (having the appropriate commands for individual robots to execute the movements and trajectories associated with a procedure, activity, surgeme, or dexeme), can be exported in varies data structures and formats. For example, exported files may be structured using JSON or XML, to allow the file to be human readable and editable outside of the above-described editor. Such files may also be encrypted or otherwise secured for transmission between different systems, or storage.

As suggested above, virtual models of a patient-specific anatomy may be utilized in various aspects of the present disclosure. For example, these models may be used to plan robotic procedures, as virtual sensors for predicting the patient's tissues in simulation or an actual procedure, act as a blueprint for creating a 3D print of the anatomical feature with correct properties, and the like. These models may derive from medical imaging data collected for a given patient and be further defined by characteristics (e.g., embodied as variable-driven formulas) such as deformation, elasticity, or cutting elements.

Figure 16:
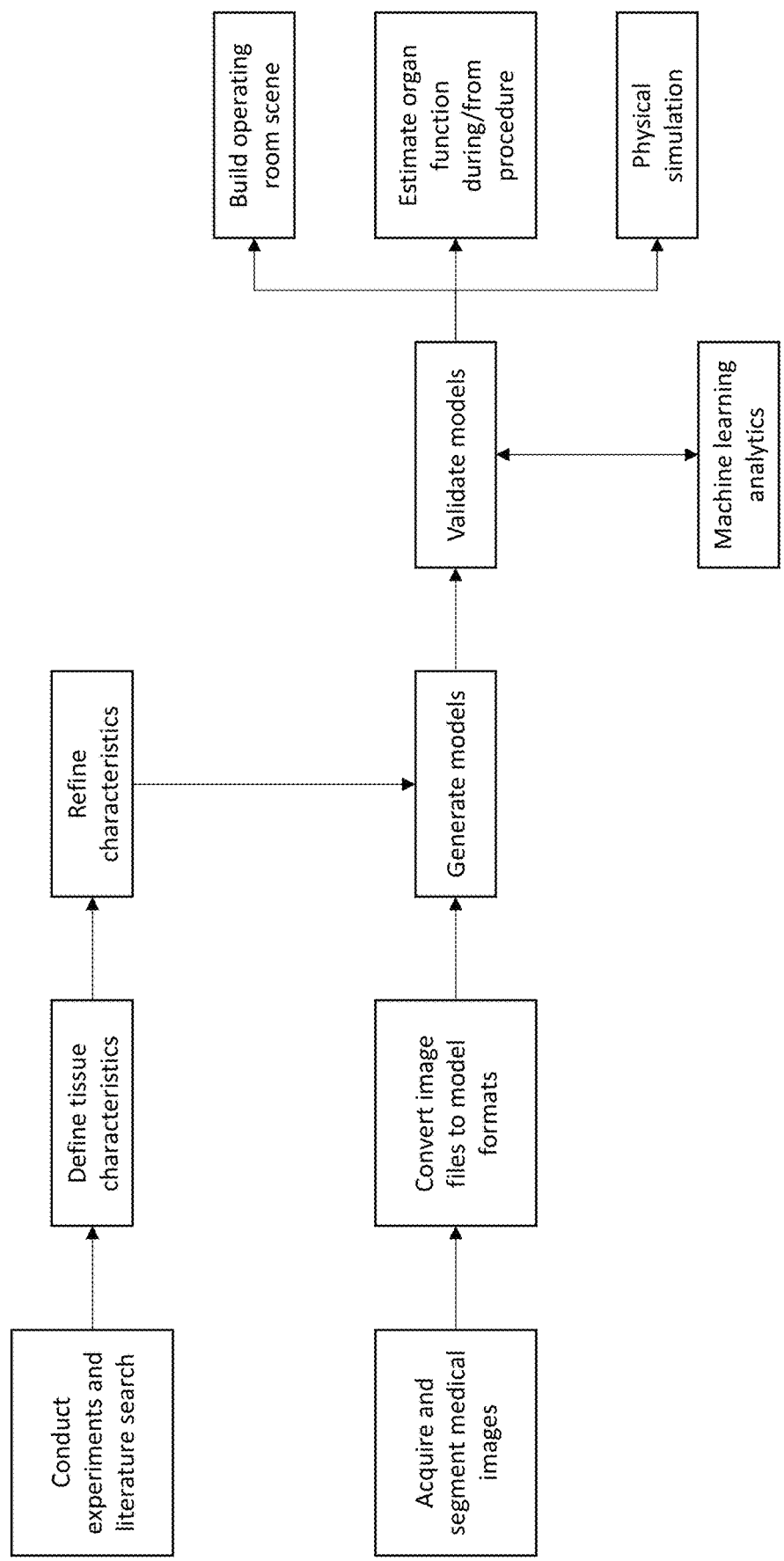
FIG. 16 illustrates an example process for achieving the proper scale and accuracy for a virtual model of patient-specific anatomy.

Achieving the proper scale and accuracy of the model can be achieved according to the example process of FIG. 16. Briefly, the process includes collecting data from experiments, literature, imaging, and the like to establish a baseline and particular characteristics of the anatomical tissue (e.g., ranges of appropriate values) from which, the model can be derived. The model may then be generated and validated. Finally, the model may be used for preparation and analysis of the surgical procedure, including for example, building an operating scene, estimating tissue function, and performing physical simulations.

More particularly the first steps involve data and image collection to understand the physical laws and characteristics that should govern the. In other words, this data may provide a baseline from which the virtual model can be derived from. This is because the human body has many tissues, each having their own set of properties that define how it reacts to external stimuli. For example, a kidney includes at least the following types of tissues: medulla, cortex, artery, vein, ureter, and collecting system. Each tissue may have different characteristics (e.g., thickness, elasticity, strength, color, density, friction coefficients, changes due to cuts, deformation characteristics, and the like), which further vary from patient to patient, and further can vary based on the tissue's and/or patient's orientation. Due to this, the initially collected data may be used to derive a range of values for each of a set of desired characteristic of the tissue, including in a plurality of directions for the orientations of interest. This data may be collected experimentally (including of the tissue itself and its interactions with various surgical instruments), literature studies, medical imaging, and the like; and may represent the specific patient and/or a general population. Such data may include the forces needed to cause a tissue to change shape in a given direction, represent how the material changes shape when a given force is applied, determine the resistance (e.g., mechanical or electrical) of the tissue when cut in a given direction, determine a spring constant for each direction of the tissue, and/or determine how the tissue reacts when cut in a given direction.

Each characteristic of the tissue may be itself modeled as a function of one or more variables. Using the noted elastic constant as an example, an elasticity characteristic may be modeled as $f(k, x)=kx$ where $f(k,x)$ represents an applied force over a distance x, and k is the elasticity constant of the tissue. The collected data may be used to then identify a range of values for the elasticity constant k.

Once the desired characteristics (and their ranges) are determined, they may be refined for example through wet and dry lab conducting more targeted studies on the characteristics of the tissues. These studies may give a better representation of how the tissues react to tools commonly used in a procedure. Iteratively refining the characteristics can improve their accuracy.

The acquired medical images may include those from any modality, such as CT, MRI, ultrasound, and the like. Once acquired, the images may be segmented to identify different types of tissues in the imaged anatomy. The segmented images may then be saved and converted to model formats, such as STL, OBJ, STEP, and the like.

With the characteristics defined and the basic visual model shapes generated, the characteristics (and associated models) are applied to the basic visual models, thereby giving the visual models physical properties and characteristics of the actual tissues. Using the kidney example from above, the medulla and cortex regions of an MR volume of a kidney may be segmented out and separately converted/saved as 3D models. Because the MR volume is taken from the patient, the resulting 3D models thus match the patient-specific anatomy. Further, the elasticity and other characteristic models associated with each segmented region may then be applied to those segmented models. Accordingly, when ultimately recombined to form a full model of the kidney, the voxels associated with medulla may be treated as having an elasticity coefficient representative of the patient's medulla, and the voxels of the cortex region of the full kidney model may have a patient-specific cortex elasticity coefficient that is different than that of the medulla. Similarly, deformability characteristics, characteristics relating to how the tissue interacts with various surgical instruments, and other characteristics of interest may be applied to each model.

Once model generation is completed, the model is validated and exact characteristic values may be determined. In one embodiment, validation occurs with a network of sensors The next step can utilize a network of sensors to validate the virtual model to set the variable's exact value for all formulas. For example, the sensors may measure an actual response of the tissue to a stimulus, and compare the actual response to the response output by the model. If the model output is within a predetermined range of the actual response, the model may be considered verified.

The final model may then be used in manner, such as those described above. For example, the model can be used to build an operating room scene, analyzed to estimate organ function due to a procedure, or build physical models for simulations. Additionally, a trained machine learning system may be utilized to continually update the model (e.g., in real time). For example, the machine learning system may be trained to receive sensor data during a procedure, and adjust characteristics of the model according to any changes in received sensor data. Therefore, as the body is changing throughout the procedure, so can the virtual model.

As noted above, one element of the pre-operative planning process may include generating an operating room scene. Each operating room scene may be specific to a room, patient, and/or procedure. Thus, in some embodiments, each operating room scene may be generated from scratch. However, because many procedures may share commonalities (e.g., be performed in the same room, with fixed structures), each operating room scene may also be based on predefined templates.

When generating a new scene, a user may first start by defining a floorplan corresponding to the operating room. The dimensions of the floorplan can include the wall lengths, corner angles, and wall heights. That is, the floor plan may be in two or three dimensions. This floorplan acts as the ultimate boundaries that all objects must lie within.

After the room boundaries are defined, the user can populate the room with operating room objects. These objects may have static positions, such as furniture (e.g., tables, cabinets, chairs), or dynamic positions, such as people, devices and machines (e.g., robots, end-effectors) that are expected to move throughout a procedure. Each model within the scene can have a predefined zone around it to prevent collisions. Each zone can be specific to the individual models and changed by the user for each model's instance.

Each object populating the room may have its own 2D or 3D model, which may be predefined or generated specifically for the scene. Additionally, the element may be represented by a generic model or one with exacting dimensions to the actual element that will be in the operating room. In addition to having appropriate dimensions, models for dynamic objects may also have appropriate physical properties such as defined joints and motion abilities. All models may be positioned relative to a room origin, such that all of the models are in a common coordinate system and are scalable.

A populated operating room scene may then be input to a machine learning system trained to output an optimized scene or suggestions for optimizing the scene. For example, the machine learning system may recognize that two robots of a user-defined scene are located in too close proximity with each other, thereby increasing the chances of collision and the need for inefficient collision avoidance movements. Accordingly, the machine learning system may output optimized locations for each robot that avoid such collision problems. Such a machine learning system may also be trained with information relating to specific procedures. For example, an orientation of multiple robots within an operating scene may be optimized for one procedure, but problematic for another procedure. By considering the specific movements of the robots associated with the procedure for which the operating room scene is being designed, the machine learning system can generate procedure- and room-specific scenes. This trained machine learning system (and/or the optimization generally) may be applied iteratively. For example, an initial scene may be generated and optimized and used in a simulation during a pre-operative planning (e.g., such as those discussed above) in which a movement error (e.g., singularity, positional error, joint limit, and the like) is recorded. That error may then be input into the trained machine learning system to further optimize the scene to remove the error. Similarly, and as discussed earlier, the machine learning system may be trained with past operation data. Thus, the outputs of the machine learning system can also be based on operating room scenes used in prior procedures, and their outcomes.

As noted above, each object in the operating room scene may be static or dynamic, and have defined zones to prevent collisions. For example, the user can place two identical tables in a scene, each instance having a different zone based on the space where it is located. During a procedure or simulation, when another object within the scene enters this zone, a warning may be generated to communicate to the moving objects that a collision is imminent. When the warning is triggered, appropriate actions may be taken such as repositioning the moving object to exit the warning zone or slowing down the speed of the moving object to minimize damage if a collision occurs.

Figure 17:
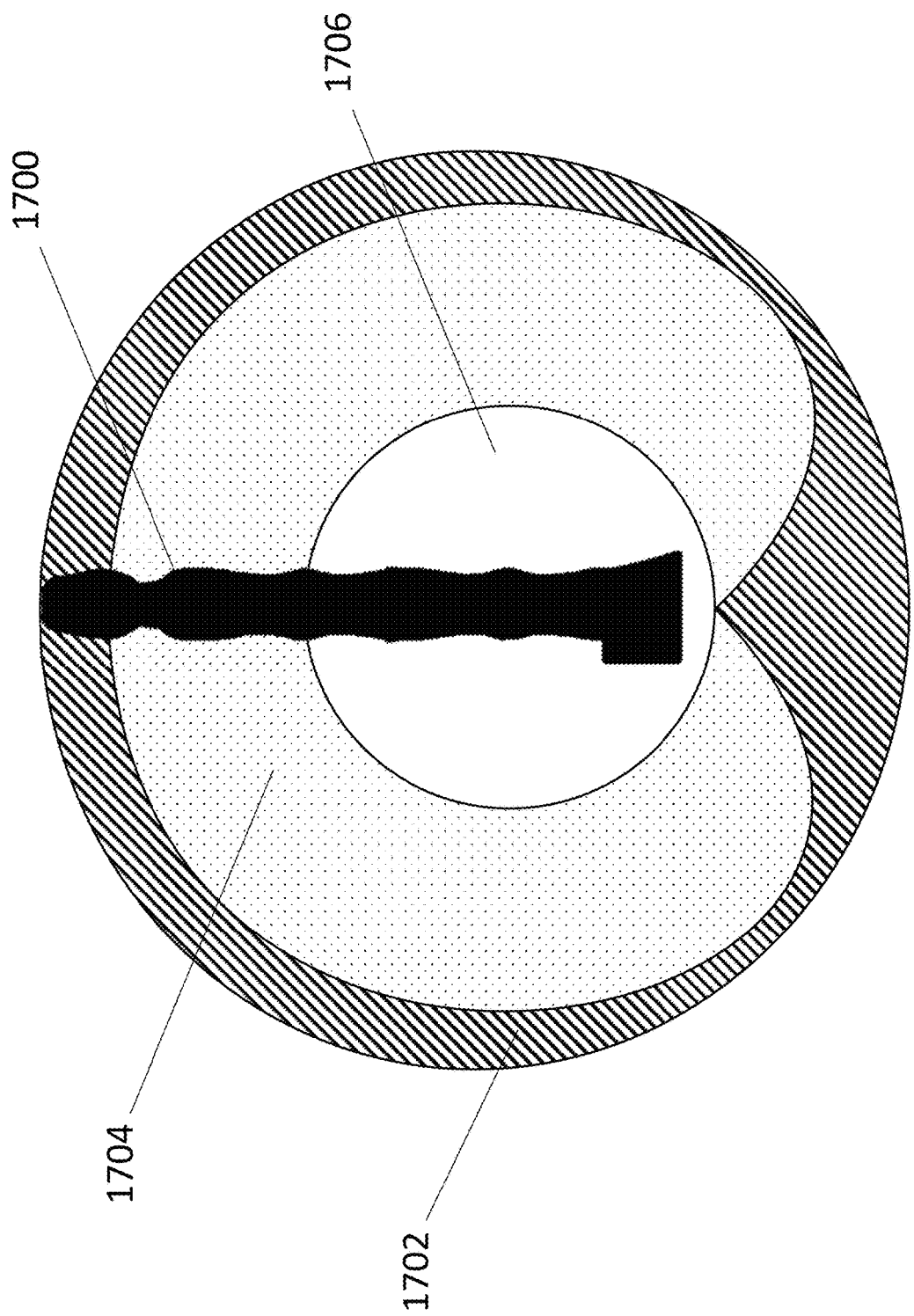
FIG. 17 illustrates full range and functional workspace areas of robots and end-effectors.

Robot and end-effectors are specific dynamic models that have unique properties. With reference to FIG. 17, a model's movement is categorized within two types of zones—full range and functional workspace. The full range of a robot 1700 can be defined as every possible location 1702 that the robot 1700 can move. The functional range 1704 is the area within the full-range 1702 where the robot 1700 can operate without running into problematic positions, like mathematical singularities or joint limits. Characteristics like Denavit-Hartenberg parameters and linkage length determined from the Denavit-Hartenberg parameters help define these separate zones. Finally, the region 1706 within the functional range 1704, and outside of the full range 1702, represents area unreachable by the robot 1700.

Dedicated safety zones may also be defined around personnel to help ensure the safety of any person in the operating room as they or dynamic objects move. The safety zones may have one or more layers. In one example, an outer layer (having the greatest distance of the safety zone around the personnel) is designated as a warning zone, while an inner layer (having a shorter distance around the personnel than the outer layer) is designated as an error zone. If any feature of any piece of equipment enters the warning layer (either by its movement or the personnel's movement), the surgical system may be configured to reduce the device's operational speed to avoid collision. If any portion of a device enters the error layer, then the system may be configured to enter into an emergency stopped state to protect the personnel working with the equipment and the patient. Each personnel model can have the ability to customize the "Safety Zone." An Example of these zones can be seen below in FIG. 9. These zones can also be utilized by the AI tools.

With a finalized operating room scene, motion profiles and trajectories may be finally determined and optimized for each robot used in a surgical procedure. For example, as discussed above with respect to the pre-operative planning framework, once the system is aware of the relative positions of each robot (and other objects in the operating room), proper trajectories can be determined that avoid collisions and sufficiently and safely perform the designed procedure.

While various features are presented above, it should be understood that the features may be used singly or in any combination thereof. Further, it should be understood that variations and modifications may occur to those skilled in the art to which the claimed examples pertain. Still further, while some aspects described above have been with reference to the kidney or prostate, it is understood that the features herein may be applied to any organ, including but not limited to, kidneys, prostates, livers, lungs, hearts, and the like.

What is claimed is:

1. A surgical system comprising:
  an imaging system configured to obtain real time intraoperative images of a patient's soft tissue organ;
  at least one controller configured to generate a rendered virtual model overlayed on to the real time intraoperative images; and
  a display configured to display the rendered virtual model overlayed on to the real time intraoperative images,
  wherein the rendered virtual model includes a predefined avoidance region within an anatomy of the patient rendered in a first visual manner, and a predefined acceptable region within the anatomy of the patient rendered in a second visual manner.

2. The surgical system of claim 1, wherein the rendered virtual model includes a surgical path rendered in the second visual manner or in a third visual manner.

3. The surgical system of claim 2, wherein the at least one controller is further configured to include a cut margin in the rendered virtual model.

4. The surgical system of claim 1, further comprising a surgical robot, wherein the at least one controller is further configured to determine a location of a surgical instrument of the surgical robot relative to the anatomy of the patient.

5. The surgical system of claim 4, further comprising an output device, wherein the at least one controller is further configured to alert a surgeon via the output device when the location of the surgical instrument is within a predetermined range of the avoidance region.

6. The surgical system of claim 4, wherein the at least one controller is further configured to control the surgical robot to avoid the avoidance region when the location of the surgical instrument is within a predetermined range of the avoidance region.

7. The surgical system of claim 1, further comprising:
  a first robotic surgical tool; and
  a second robotic surgical tool,
  wherein the at least one controller is further configured to:
    receive a predefined avoidance region within an anatomy of a patient;
    receive a real-time location of the first surgical tool;
    receive a real-time location of the second surgical tool;
    receive a predefined surgical space outside of the patient; and
    provide an error warning based upon a real-time location of the second surgical tool relative to the avoidance region, the real-time location of the first surgical tool, and the predefined surgical space outside of the patient.

8. The surgical system of claim 7, wherein the error warning provides a remedial action to avoid a collision of the second surgical tool with the avoidance region, first surgical tool and/or the predefined surgical space.

9. The surgical system of claim 8, comprising an imaging system obtaining real time intraoperative images of a soft tissue organ of a patient and the virtual model of at least a part of one of the first robotic surgical tool and second robotic surgical tool superimposed on the real time intraoperative image.

10. A surgical system comprising:
  a first robotic surgical tool;
  a second robotic surgical tool; and
  at least one controller configured to:
    receive a predefined avoidance region within an anatomy of a patient;
    receive a real-time location of the first surgical tool;
    receive a real-time location of the second surgical tool;
    receive a predefined surgical space outside of the patient; and
    provide an error warning based upon a real-time location of the second surgical tool relative to the avoidance region, the real-time location of the first surgical tool, and the predefined surgical space outside of the patient.

11. The surgical system of claim 10, wherein the error warning provides a remedial action to avoid a collision of the second surgical tool with the avoidance region, first surgical tool and/or the predefined surgical space.

12. The surgical system of claim 11, comprising an imaging system obtaining real time intraoperative images of a soft tissue organ of a patient and the virtual model of at least a part of one of the first robotic surgical tool and second robotic surgical tool superimposed on the real time intraoperative image.

* * * * *